US006528245B2

(12) United States Patent
Sanchez-Ramos et al.

(10) Patent No.: US 6,528,245 B2
(45) Date of Patent: *Mar. 4, 2003

(54) BONE MARROW CELLS AS A SOURCE OF NEURONS FOR BRAIN AND SPINAL CORD REPAIR

(75) Inventors: Juan Sanchez-Ramos, Tampa, FL (US); Shijie Song, Tampa, FL (US); William Janssen, Tampa, FL (US); Paul Sanberg, Spring Hill, FL (US); Thomas Freeman, Tampa, FL (US)

(73) Assignee: University of South Florida, Tampa, FL (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/307,824

(22) Filed: May 7, 1999

(65) Prior Publication Data

US 2002/0146821 A1 Oct. 10, 2002

Related U.S. Application Data

(60) Provisional application No. 60/084,533, filed on May 7, 1998, provisional application No. 60/112,979, filed on Dec. 17, 1998, and provisional application No. 60/129,684, filed on Apr. 16, 1999.

(51) Int. Cl.$^7$ .............................. A01N 1/02; C12N 5/00; C12N 5/02; C12N 5/08

(52) U.S. Cl. .................... 435/1.1; 435/368; 435/325

(58) Field of Search ...................... 424/184.1; 435/325, 435/368, 1.1

(56) References Cited

U.S. PATENT DOCUMENTS

| | | | |
|---|---|---|---|
| 4,714,680 A | 12/1987 | Civin | 435/240 |
| 5,087,570 A | 2/1992 | Weissman | 435/240 |
| 5,516,977 A | 5/1996 | Ford | 800/2 |
| 5,538,713 A | 7/1996 | P eault | 424/9.2 |
| 5,580,777 A | 12/1996 | Bernard | 435/240.2 |
| 5,633,426 A | 5/1997 | Namikawa | 800/2 |
| 5,665,557 A | 9/1997 | Murray | 435/7.24 |
| 5,690,927 A | 11/1997 | Major | 424/93.21 |
| 5,753,491 A | 5/1998 | Major | 435/240.2 |
| 5,753,505 A | 5/1998 | Luskin | 435/375 |
| 5,753,506 A | 5/1998 | Johe | 435/377 |
| 5,759,793 A | 6/1998 | Schwartz | 435/7.24 |
| 5,843,780 A | 12/1998 | Thomson | 435/363 |

FOREIGN PATENT DOCUMENTS

| | | | | |
|---|---|---|---|---|
| WO | WO 99/43286 A2 | 9/1999 | | A61K/35/00 |
| WO | WO 99/43286 A3 | 12/1999 | | A61K/35/00 |

OTHER PUBLICATIONS

Kandel, Principles of Neural Science, Elsevier p. 213–224 and 891–99, 1991.*
Alberts, Molecular Biology of the Cell, Garland Pub., p. 973–81, 1989.*
Nakajima et al., Blood 84(12):4107–15, 1994.*
Gattei et al., Blood 89(8):2925–37, 1997.*
Gimble et al., Blood 74(1):303–311, 1989.*
Kaufman and Barnett, Serum Factor Supporting Long–Term Survival of Rat Central Neurons in Culture. Science vol. 220, 1983.
Weinstein, Shelanski, and Leim. C17, A Retrovirally Immortalized Neuronal Cell Line, Inhibits the Proliferation of Astrocytes and Astrocytoma Cells by a Contact– Mediated Mechanism. GLIA 3:130–139 (1990).
Pereira, Halford, O'Hara, Leeper, Sokolov, Pollard, Bagasra, Prockop. Cultured adherent cells from marrow can serve as long–lasting precursor cells for bone, cartlige, and lung in irradiated mice, Proc. Natl. Acad.. Sci . USA vol. 92, pp. 4857–4861, May 1995.
Pereira, Hume, Halford, Prockop. Bone fragility in transgenic mice expressing a mutated gene for type I procollagen (COL1A1) parallels the age–dependent phenotype of human osteogensis imperfecta. J Bone Miner Res, Dec. 1995, 10:12, 1837–43.
Pereira, Halford, O'Hara, Pollard, Volpe, Laptev, Prockop. Use of Marrow Stromal Cells to Replace Bone Cells in a Transgenic Mouse Model for Osteogenesis Imperfecta. Matrix Bioloby Jourlan of the International Society for Matrix Biology, vol. 15, No. 3, pp. 188, Sep. 1996.
Darwin J. Prockop, Marrow Stromal Cells as Stem Cells for Nonhematopoietic Tissues. Science vol. 276, Apr. 4, 1997. pp. 71–74.
Pereira, O'Hara, Laptev, Halford, Pollard, Class, Simon, Livezey, Prockop. Marrow stromal cells as a source of progenitor cells for phenotype of osteogenesis imperfecta. Prco. Natl. Acad. Sci. USA, vol. 95 pp. 1142–1147, Feb. 1998.

(List continued on next page.)

*Primary Examiner*—Gary Kunz
*Assistant Examiner*—Sharon Turner
(74) *Attorney, Agent, or Firm*—Sierra Patent Group, Ltd.; Barbara J. Luther

(57) ABSTRACT

Bone marrow stromal cells (BMSC) differentiate into neuron-like phenotypes in vitro and in vivo, engrafted into normal or denervated rat striatum. The BMSC did not remain localized to the site of the graft, but migrated throughout the brain and integrated into specific brain regions in various architectonic patterns. The most orderly integration of BMSC was in the laminar distribution of cerebellar Purkinje cells, where the BMSC-derived cells took on the Purkinje phenotype. The BMSC exhibited site-dependent differentiation and expressed several neuronal markers including neuron-specific nuclear protein, tyrosine hydroxylase and calbindin. BMSC can be used to target specific brain nuclei in strategies of neural repair and gene therapy.

5 Claims, 9 Drawing Sheets

(6 of 9 Drawing Sheet(s) Filed in Color)

OTHER PUBLICATIONS

Azizi, Stokes, Augelli, diGirolamo, Prockop. Engraftment and migration of human bone marrow stromal cells implanted in the brains of albino rats–similatities to astrocyte grafts.Proc. Natl. Acad. Sci USA. vol. 95, pp 3908–3913. Mar. 1998.

Elliot Marshall, A Versatile Cell Line Raises Scientific Hopes, Legal Questions, Science vol. 282, Nov. 6, 1998. pp 1014–1015.

Bone Marrow Cells May Provide Muscle Power, Science Mar. 6, 1998.

Ferrari, De Angelis, Coletta, Paolucci, Stornaiuolo, Cossu, Mavilio. Muscle Regeneration by Bone Marrow– Derived Myogenic Progenitors. Science vol. 279 Mar. 6, 1998. pp. 1528–1530.

Sanchez, Cardozo–Pelaez, Differentiation of Neuron–like Cells from Bone Marrow Stomal Cells. Movement Disorders, vol. 13, Supplement 2, 1998.

Thomson, Itskovitz–Eldor, Shapiro, Waknitz, Swiergiel, Marshall, Jones, Embryonic StemCell Lines Derived from Human Blastocysts. Scirnce vol .282 Nov. 6, 1998. pp. 1117–1125.

Florence, Taub, Kaas. Large Scale Sprouting of Cortical Connections After Peripheral Injury in Adult Macaque Monkeys. Science vol. 282 Nov. 6, 1998.

Marcia Barinaga, New Leads to Brain Neuron Regeneration. Science vol. 282 Nov. 6, 1998. pp 1018–1019.

Elliot Marshall, A Versatile Cell Line Raises Scientific Hopes, Legal Questions, Science vol. 282, Nov. 6, 1998. pp 1014–1015.

S. Walkley et al., "Bone marrow transplantation corrects the enzyme defect in neurons of the central nervous system in a lysosomal storage disease", *Proc. Natl. Acad. Sci. USA*, vol. 91, pp. 2970–2974, Apr. 1994.

* cited by examiner

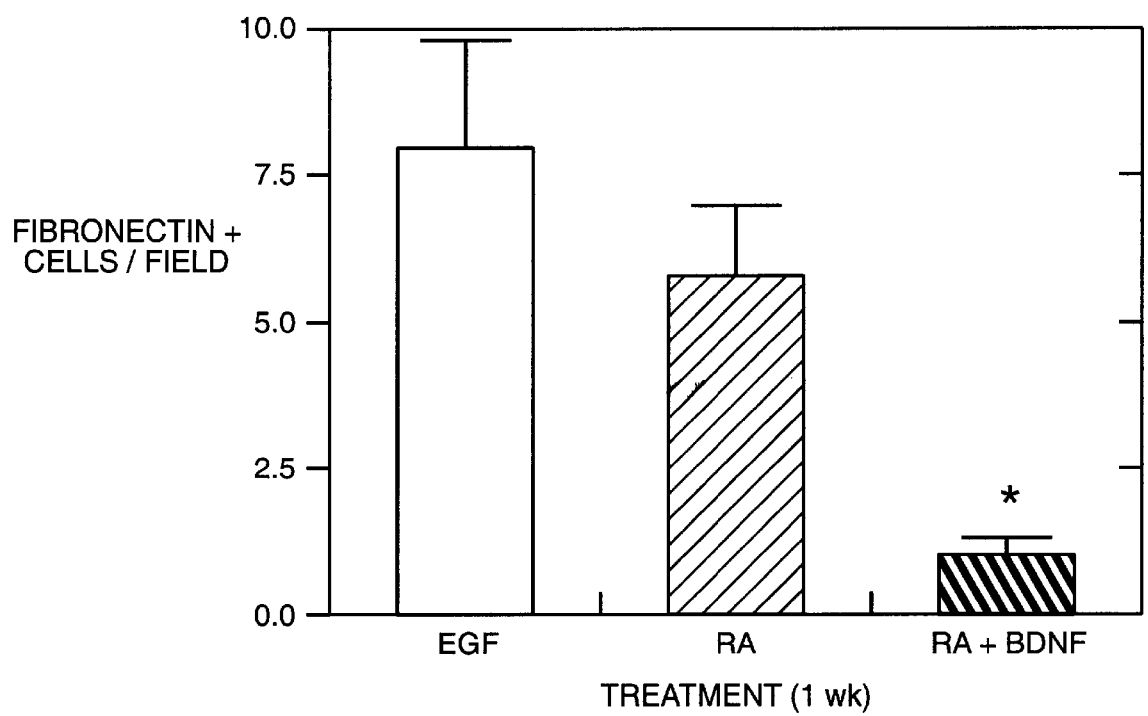
FIG._1

FIG._2A FIG._2B
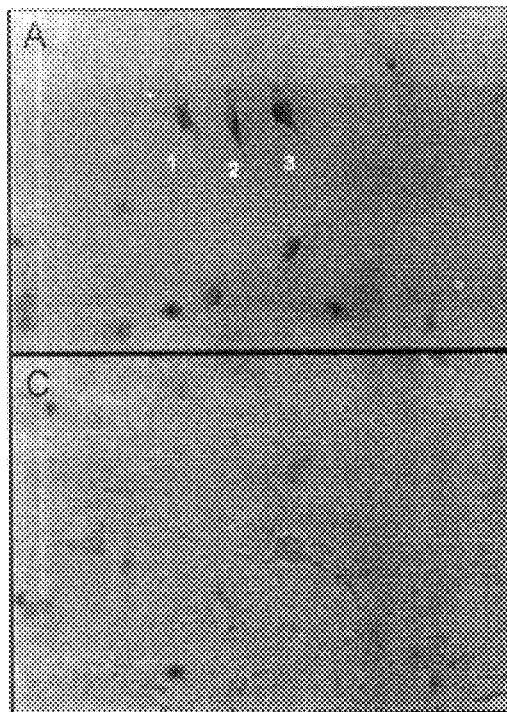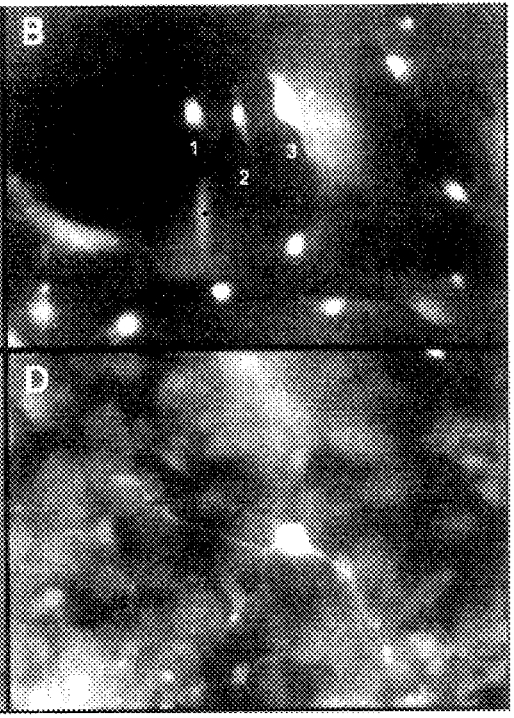
FIG._2C FIG._2D
FIG._2E FIG._2F
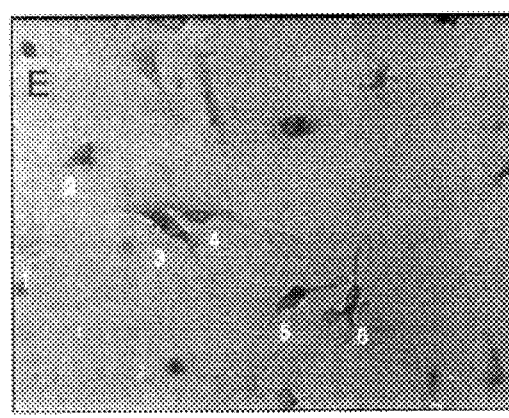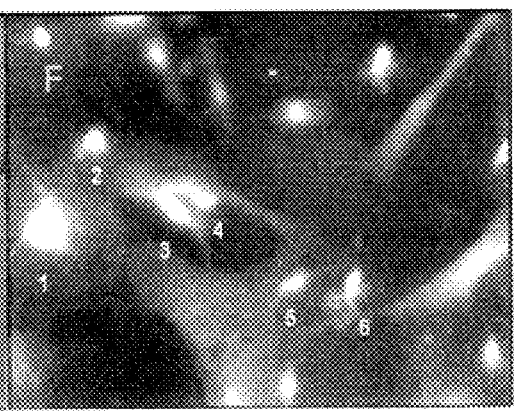

FIG._3A
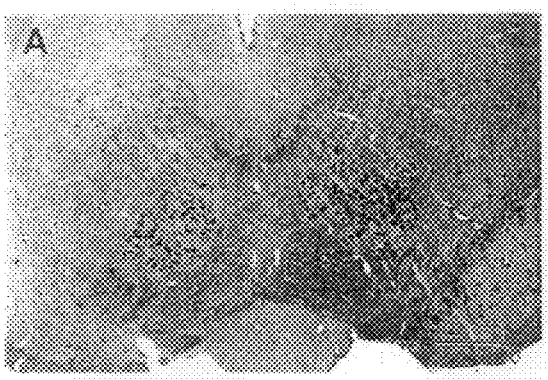
FIG._3B
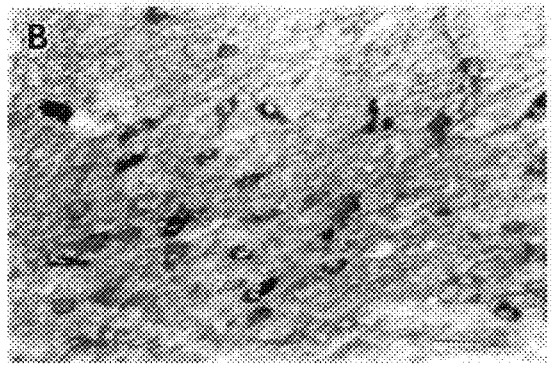
FIG._3C
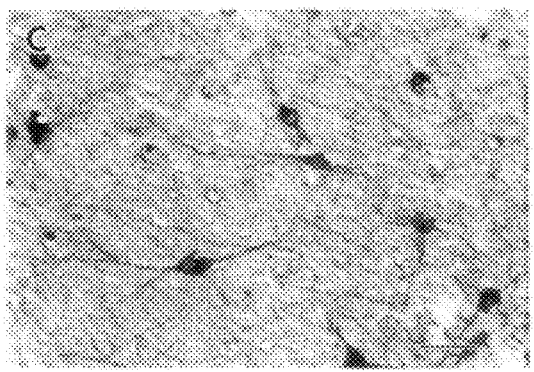
FIG._3D
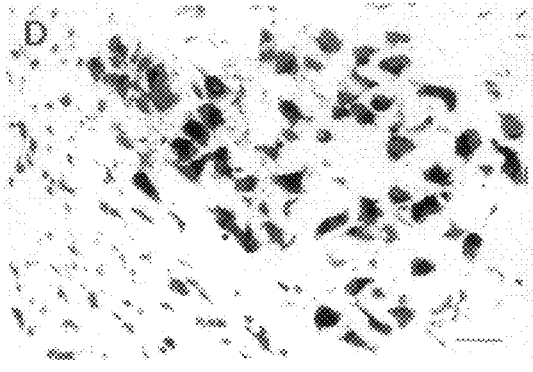

FIG._3E
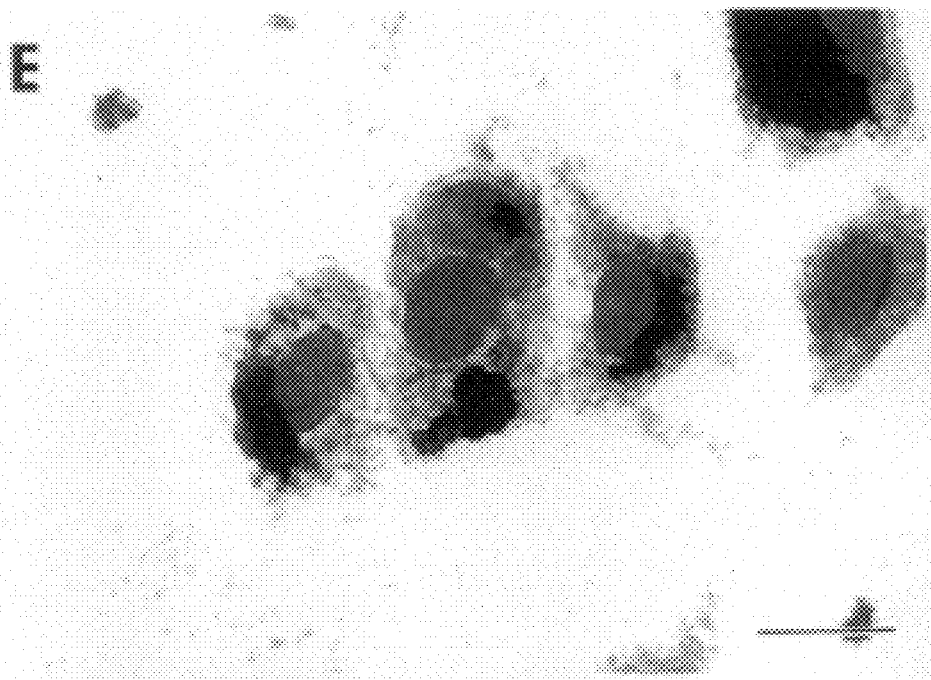
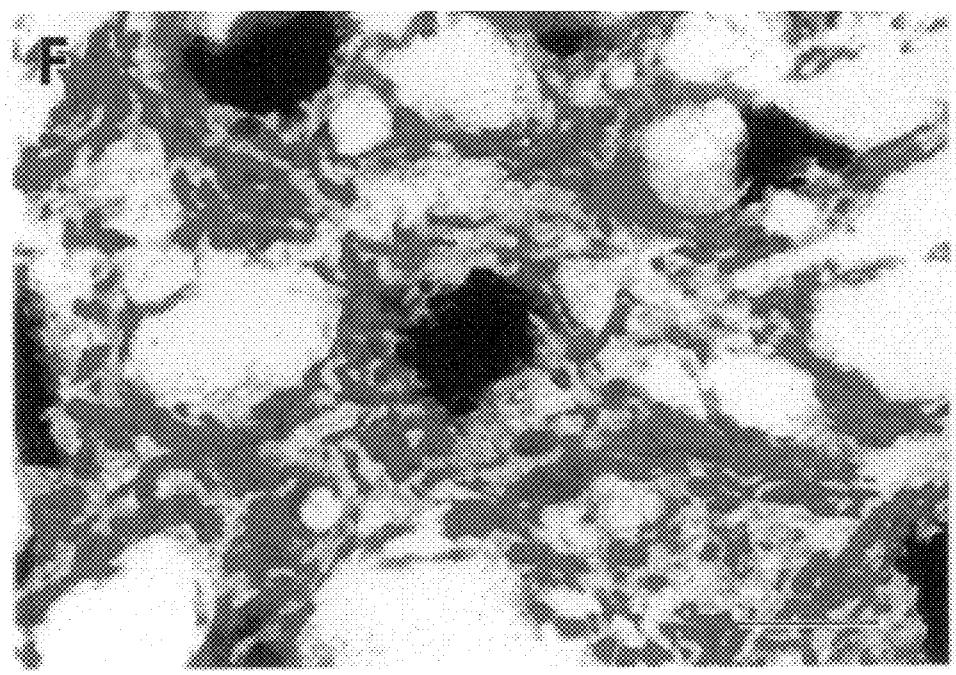
FIG._3F

FIG._4A
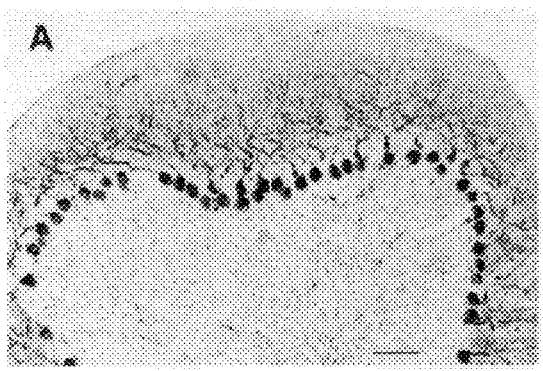
FIG._4C
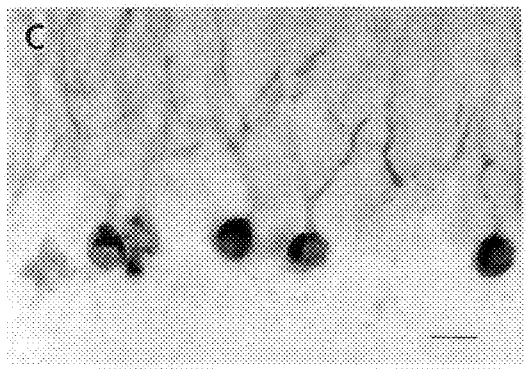
FIG._4B
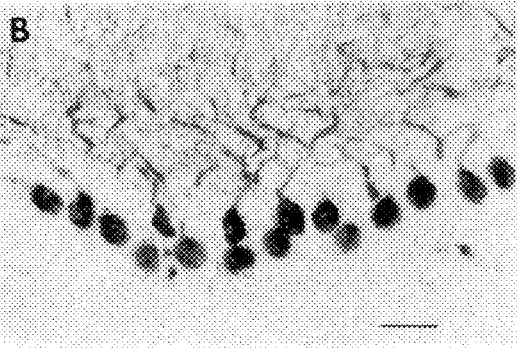
FIG._4D
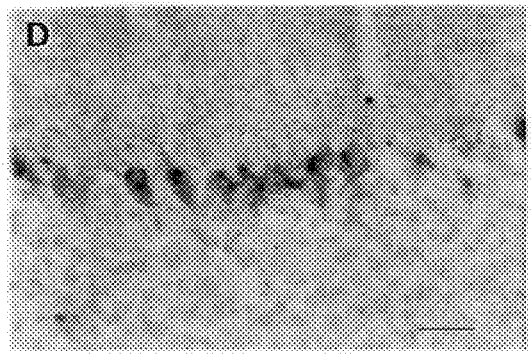

FIG._4E
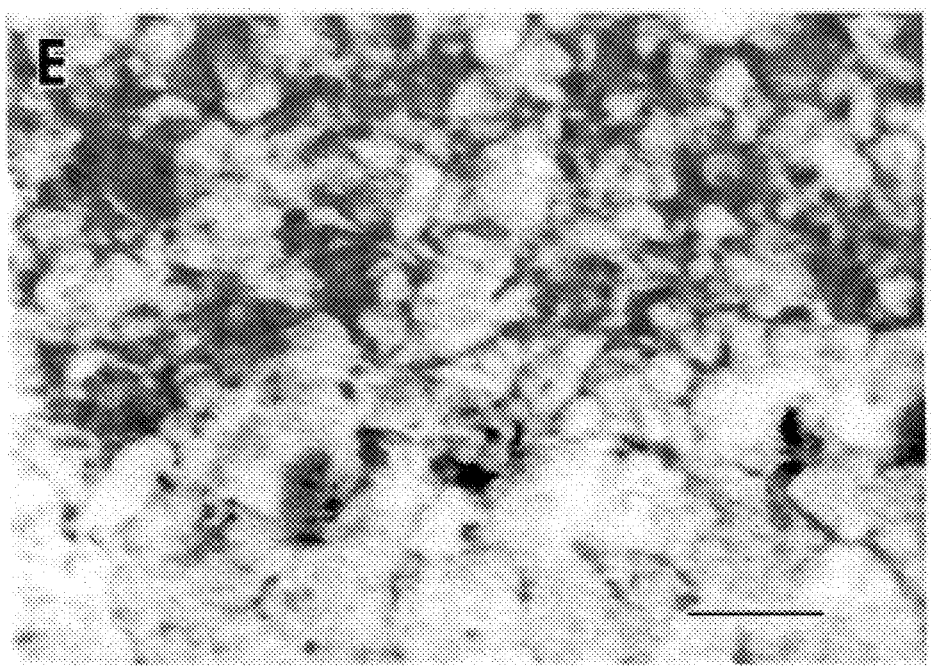
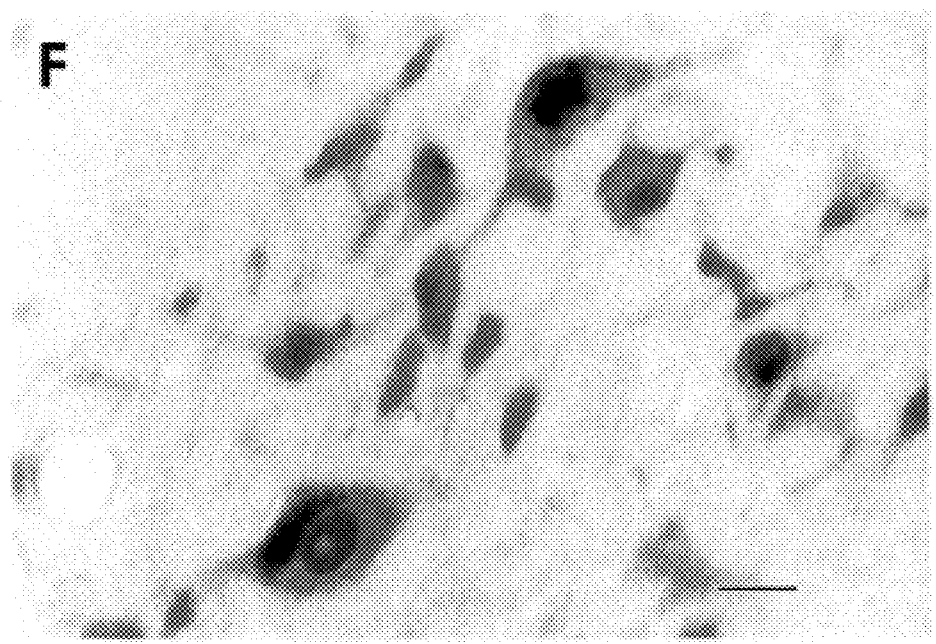
FIG._4F

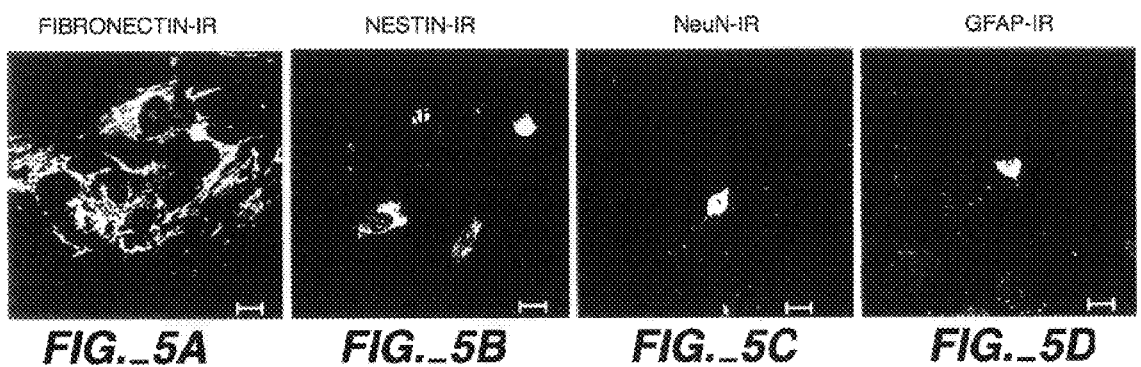
FIG._5A  FIG._5B  FIG._5C  FIG._5D
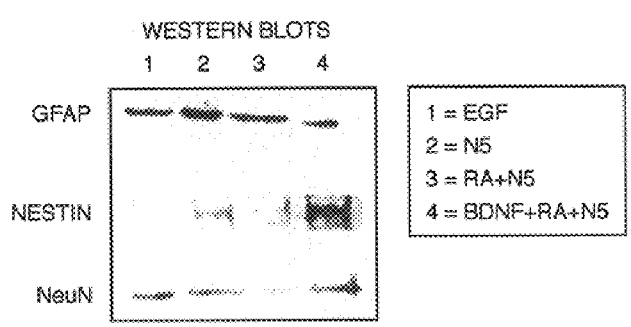
FIG._6

CO-CULTURES OF HUMAN BSC AND FETAL RAT STRIATAL CELLS
FIG._7A
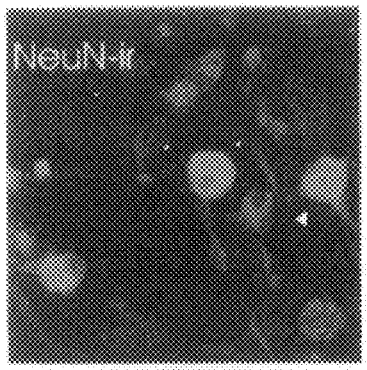
FIG._7C
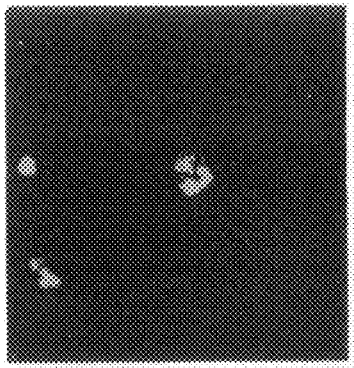
FIG._7E
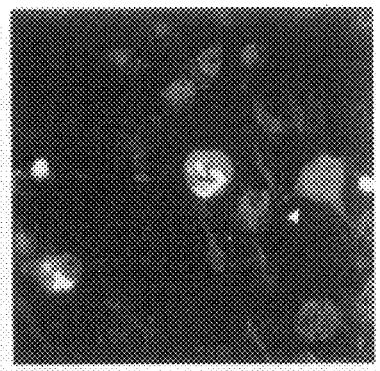
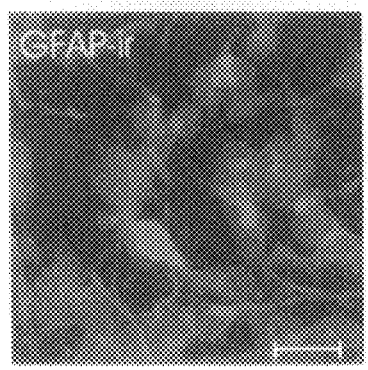
FIG._7B
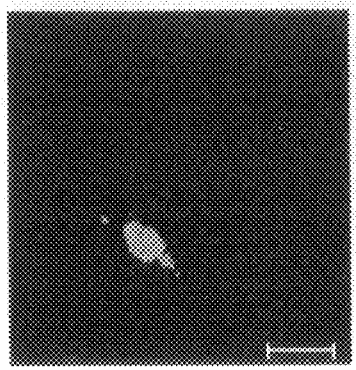
FIG._7D
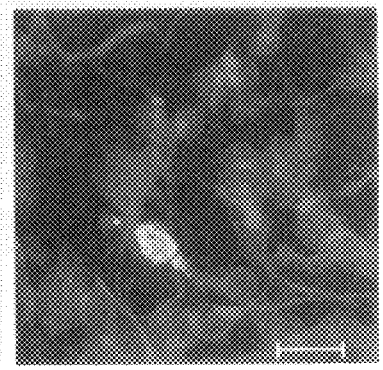
FIG._7F

FIG._8
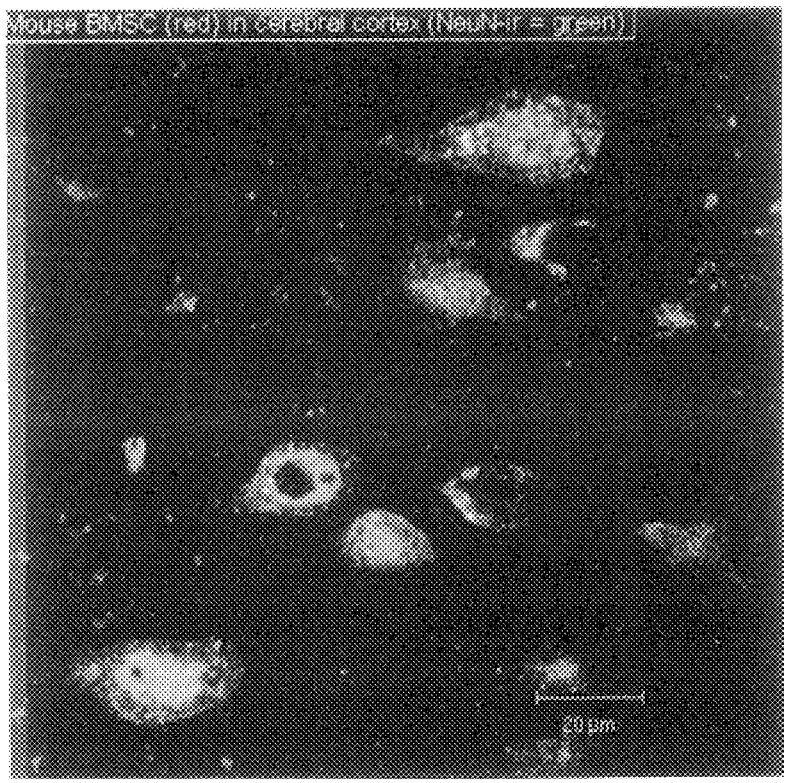
FIG._9

BONE MARROW CELLS AS A SOURCE OF NEURONS FOR BRAIN AND SPINAL CORD REPAIR

RELATED APPLICATIONS

This application claims the benefit of U.S. Provisional Application No. 60/084,533, filed May 7, 1998; U.S. Provisional Application No. 60/112,979, filed Dec. 17, 1998; and U.S. Provisional Application No. 60/129,684 filed Apr. 16, 1999.

BACKGROUND

1. Field of Use

This application relates to methods of culturing bone marrow cells such that they express neuronal phenotype for use in transplantation.

2. Background Information

Neurobiologists have long considered the neurons in the adult brain to be like a precious nest egg: a legacy that dwindles with time and illness and is difficult if not impossible to rebuild. Parkinson's and Alzheimer's are examples of neurodegenerative diseases whose cures await scientists overcoming the difficulty of rebuilding neurons in the human adult brain. Parkinson's disease (PD), is a disorder of middle or late life, with very gradual progression and a prolonged course. HARRISON'S PRINCIPLES OF INTERNAL MEDICINE, Vol. 2, 23d ed., Ed. by Isselbacher, Braunwald, Wilson, Martin, Fauci and Kasper, McGraw-Hill Inc., New York City, 1994, pg. 2275. The most regularly observed changes have been in the aggregates of melanin-containing nerve cells in the brainstem (substantia nigra, locus coeruleus), where there are varying degrees of nerve cell loss with reactive gliosis (most pronounced in the substantia nigra) along with distinctive eosinophilic intra-cytoplasmic inclusions. (Id. at 2276).

In its fully developed form, PD is easily recognized. The stooped posture, the stiffness and slowness of movement, the fixity of facial expression, the rhythmic tremor of the limbs, which subsides on active willed movement or complete relaxation, are familiar to every clinician. Generally, accompanying the other characteristics of the fully developed disorder is the festinating gait, whereby the patient, prevented by the abnormality of postural tone from making the appropriate reflex adjustments required for effective walking, progresses with quick shuffling steps at an accelerating pace as if to catch up with the body's center of gravity. (Id. at 2276).

Although the modem treatment of PD is more successful than any that was available before the introduction of levodopa, including stereotactic surgery, there are still many problems. (Id. at 2277). Underlying much of the difficulty undoubtedly is the fact that none of these therapeutic measures has an effect on the underlying disease process, which consists of neuronal degeneration. Ultimately, a point seems to be reached where pharmacology can no longer compensate for the loss of basal ganglia dopamine. (Id.).

Alzheimer's Disease (AD) is due to a degenerative process characterized by progressive loss of cells from the basal forebrain, cerebral cortex and other brain areas. Acetylcholine-transmitting neurons and their target nerves are particularly affected. Senile plagues and neurofibrillary tangles are present. Pick's disease has a similar clinical picture to Alzheimer's disease but a somewhat slower clinical course and circumscribed atrophy, mainly affecting the frontal and temporal lobes. One animal model for Alzheimer's disease and other dementias displays hereditary tendency toward the formation of such plaques. It is thought that if a drug has an effect in the model, it also may be beneficial in at least some forms of Alzheimer's and Pick's diseases. At present there are palliative treatments but no means to restore function.

A group of degenerative disorders characterized by progressive ataxia due to degeneration of the cerebellum, brainstem, spinal cord and peripheral nerves, and occasionally the basal ganglia. Many of these syndromes are hereditary; other occur sporadically. The spinocerebellar degenerations are logically placed in three groups: predominantly spinal ataxias, cerebellar ataxias and multiple-system degenerations. To date there are no treatments. Friedrich's ataxia is the prototypical spinal ataxia whose inheritance is autosomal recessive. The responsible gene has been found on Chromosome 9. Symptoms begin between ages of 5 and 15 with unsteady gait, followed by upper extremity ataxia and dysarthria. Patients are areflexic and lose large-fiber sensory modalities (vibration and position sense). Two other diseases have similar symptoms: Bassen-Kornzweig syndrome (abeta-lipoproteinemia and vitamin E deficiency) and Refsom's disease (phytanic acid storage disease). Cerebellar cortical degenerations generally occur between ages 30 and 50. Clinically only signs of cerebellar dysfunction can be detected, with pathologic changes restricted to the cerebellum and occasionally the inferior olives. Inherited and sporadic cases have been reported. Similar degeneration may also be associated with chronic alchoholism.

In multiple-system degenerations, ataxia occurs in young to middle adult life in varying combinations with spasticity and extrapyramidal, sensory, lower motor neuron and autonomic dysfunction. In some families, there may also be optic atrophy, retinitis pigmentosa, opthalmoplegia and dementia.

Another form of cerebellar degeneration is paraneoplastic cerebellar degeneration that occurs with certain cancers, such as oat cell lung cancer, breast cancer and ovarian cancer. In some cases, the ataxia may precede the discovery of the cancer by weeks to years. Purkinje cells are permanently lost, resulting in ataxia. Even if the patient is permanently cured of the cancer, their ability to function may be profoundly disabled by the loss of Purkinje cells. There is no specific treatment.

Strokes also result in neuronal degeneration and loss of functional synapses. Currently there is no repair, and only palliation and rehabilitation are undertaken.

Neurotransplantation has been used to explore the development of the central nervous system and for repair of diseased tissue in conditions such as Parkinson's and other neurodegenerative diseases. The experimental replacement of neurons by direct grafting of fetal tissue into the brain has been accomplished in small numbers of patients in several research universities (including our University of South Florida); but so far, the experimental grafting of human fetal neurons has been limited by scarcity of appropriate tissue sources, logistic problems, legal and ethical constraints, and poor survival of grafted neurons in the human host brain.

One method replaces neurons by using marrow stromal cells as stem cells for non-hematopoietic tissues. Marrow stromal cells can be isolated from other cells in marrrow by their tendency to adhere to tissue culture plastic. The cells have many of the characteristics of stem cells for tissues that can roughly be defined as mesenchymal, because they can be differentiated in culture into osteoblasts, chondrocytes, adipocytes, and even myoblasts. Therefore, marrow stromal cells present an intriguing model for examining the differentiation of stem cells. Also, they have several characteristics that make them potentially useful for cell and gene therapy. Prockop, D.J. *Science:* 26: 71–74 (1997). This population of bone marrow cells (BMSC) have also been used to prepare dendritic cells, (K. Inaba, et al., *J. Experimental Med.* 176: 1693–1702 (1992)) which, as the name implies, have a morphology which might be confused for neurons. Dendritic cells comprise a system of antigen-presenting cells involved in the initiation of T cell responses. The specific growth factor which stimulates production of dendritic cells has been reported to be granulocyte/macrophage colony-stimulating factor (GM-CSF). K. Inaba, et al., *J. Experimental Med.* 176: 1693–1702 (1992).

The presence of stem cells for non-hematopoietic cells in bone marrow was first suggested by the observations of the German pathologist Cohnheim 130 years ago. J. Cohnheim, *Arch. Path. Anat. Physiol. Klin. Med.* 40: 1 (1867). Cohnheim studied wound repair by injecting an insoluble aniline dye into the veins of animals and then looking for the appearance of dye-containing cells in wounds he created at a distal site. He concluded that most, if not all, of the cells appearing in the wounds came from the bloodstream, and, by implication, from bone marrow. The stained cells included not only inflammatory cells but also cells that had a fibroblast-like morphology and were associated with thin fibrils. Therefore, Cohnheim's work raised the possibility that bone marrow may be the source of fibroblasts that deposit collagen fibers as part of the normal process of wound repair. The source of fibroblasts in wound repair has been examined in more than 40 publications since Cohnheim's report of 1867. See, for example, R. Ross, N. B. Everett, R. Tyler, *J. Cell Biol.* 44: 645 (1970); J. K. Moen. *J. Exp. Med.* 61: 247 (1935); N. L. Petrakis, M. Davis, S. P. Lusia, *Blood* 17: 109 (1961); S. R. S. Rangan, *Exp. Cell Res.* 46: 477 (1967); J. M. Davidson, in INFLAMMATION: BASIC PRINCIPLES AND CLINICAL CORRELATES, J. I. Gallin, I. M. Goldstein, R. Snyderman, Eds. (Raven, New York City, ed. 2, 1992, pp. 809–19; R. Bucala, L. A. Spiegel, J. Chesney, N. Hogan, A. Cerami, *Mol. Med.* 1: 71 (1994). Most of the data suggest that the fibroblasts are of local origin, but a the issue has not been resolved and is still being examined. Prockop, D. J. *Science* 26: 71–74 (1997)

Although Cohnheim's thesis has not yet been substantiated, definitive evidence that bone marrow contains cells that can differentiate into fibroblasts as well as other mesenchymal cells has been available since the pioneering work of Friedenstein, beginning in the mid-1970's. A. J. Friedenstein, U. Gorskaja, N. N. Kulagina, *Exp. Hematol.* 4: 276 (1976). Friedenstein placed samples of whole bone marrow in plastic culture dishes and poured off the cells that were nonadherent. The most striking feature of the adherent cells was that they had the ability to differentiate into colonies that resembled small deposits of bone or cartilage. Freidenstein's initial observations were extended by a number of investigators during the 1980s, particularly by Piersma and associates (A. H. Piersma, R. E. Ploemacher, k. G. M. Brockbank, *Br. J. HaematoL.* 54: 285 (1983); A. H. Piersma et al., *Exp. Hematol.* 13: 237 (1985)) and Owen and associates. C. R. Howlett et al., *Clin. Orthop. Relat. Res.* 213: 251 (1986); H. J. Mardon, J. Bee, k. von der Mark, M. E. Owen, *Cell Tissue Res.* 250: 157 (1987); J. N. Beresford, J. H. Bennett, C. Devlin, P. S. Leboy, M. E. Owen, *J. Cell Sci.* 102: 341 (1992). These and other studies (M. E. Owen and A. J. Friedenstein, in *Cell and Molecular Biology of Vertebrate Hard Tissues*, Ciba Foundation Symp. 136, Wiley, Chichester, UK, 1988, pp. 42–60; S. L Cheng et al., *Endocrinology* 134: 277 (1994); A. I. Caplan, *J. Orthop. Res.* 9: 641 (1991); D. J. Richard et al., *Dev. Biol.* 161: 218 (1994). S. Wakitani, T. Saito, and A. J. Caplan (*Muscle Nerve* 18: 1412 (1995)) demonstrated that MSCs differentiated into myoblasts and myotubes by treatment with 5-azacytidine and amphotericin B (Fungasome, Gibco). D. Phinney (Prockop, D. J. *Science.* 26: 71–74 (1997)), recently observed that the cells differentiate into myoblasts and myotubes after treatment with amphotericin B (1 µg/ml) alone; A. J. Friedenstein, R. K. Chailakahyan, U. V. Gerasimov, *Cell Tissue Kinet.* 20: 263 (1987); A. Keating, W. Horsfall, R. G. Hawley, F. Toneguzzo, *Exp. Hematol.* 18: 99 (1990); B. R. Clark and A. Keating, *Ann. N. Y Acad. Sci* 770: 70 (1995)) established that the Marrow Stromal Cells (MSCs) isolated by the relatively crude procedure of Friedenstein were multipotential and readily differentiated into osteoblasts, chondroblasts, adipocytes, and even myoblasts.

Even though the multipotential properties of MSCs have been recognized for several decades, there are surprisingly large gaps in our information about the cells themselves. The cells, isolated by their adherence to plastic as described by Friedenstein (A. J. Friedenstein, U. Gorskaja, N. N. Kulagina, *Exp. Hematol.* 4: 276 (1976)), initially are heterogeneous and difficult to clone. The fraction of the hematopoietic cells is relatively high in initial cultures of mouse marrow but is less than 30% with human marrow (M. E. Owen and A. J. Friedenstein, in *Cell and Molecular Biology of Vertebrate Hard Tissues*, Ciba Foundation Symp. 136, Wiley, Chichester, UK, 1988, pp. 42–60; S. L Cheng et al., *Endocrinology* 134: 277 (1994); A. I. Caplan, *J. Orthop. Res.* 9: 641 (1991); D. J. Richard et al., *Dev. Biol.* 161: 218 (1994); A. Keating, W. Horsfall, R. G. Hawley, F. Toneguzzo, *Exp. Hematol.* 18: 99 (1990); B. R. Clark and A. Keating, Ann. *N. Y Acad. Sci.* 770: 70 (1995)). Most of the readily identifiable hematopoietic cells are lost as the cells are maintained as primary cultures for 2 or 3 weeks. The cultured MSCs synthesize an extracellular matrix that includes interstitial type I collagen, fibronectin, and the type IV collagen and laminin of basement membranes (M. E. Owen and A. J. Friedenstein, in *Cell and Molecular Biology of Vertebrate Hard Tissues*, Ciba Foundation Symp. 136, Wiley, Chichester, UK, 1988, pp. 42–60; S. L Cheng et al., *Endocrinology* 134: 277 (1994); A. I. Caplan, *J. Orthop. Res.* 9: 641 (1991); D. J. Richard et al., *Dev. Biol.* 161: 218 (1994); A. Keating, W. Horsfall, R. G. Hawley, F. Toneguzzo, *Exp. Hematol.* 18: 99 (1990); B. R. Clark and A. Keating, *Ann. N. Y Acad. Sci.* 770: 70 (1995)). A small fraction of the cultured cells synthesize factor VII-associated antigen and therefore are probably endothelial. The cells secrete cytokines, the most important of which appear to be interleukin-7 (IL-7), IL-8, IL-11, and stem cell factor (c-kit ligand). Conditions for differentiating the cells are somewhat species-dependent and are influenced by incompletely defined variables, such as the lot of fetal calf serum used. However, MSCs from mouse, rat, rabbit, and human readily differentiate into colonies of osteoblasts (depositing mineral in the form of hydroxyapatite), chondrocytes (synthesizing cartilage matrix), and adipocytes in response to dexamethasone, 1,25-dihydroxyvitamin $D_3$, or cytokines such as BMP-2 (A. J. Friedenstein, U. Gorskaja, N. N. Kulagina, *Exp. Hematol.* 4: 276 (1976); 5–11). In response to 5-azacytidine with amphotericin B (Fungasome, Gibco) or amphotericin B alone, S. Wakitani, T. Saito, and A. J. Caplan (*Muscle Nerve* 18: 1412 (1995)) demonstrated that MSCs differentiated into myoblasts and myotubes by treatment with 5-azacytidine and amphotericin B. D. Phinney (unpublished data) recently observed that the cells differentiate into myoblasts and myotubes after treatment with amphotericin B (1 μg/ml) alone, and they differentiated into myoblasts that fuse into rhythmically beating myotubes.

Most experiments on the differentiation of MSCs have been carried out with cultures of MSCs as described by Friedenstein (A. J. Friedenstein, U. Gorskaja, N. N. Kulagina, *Exp. Hematol.* 4: 276 (1976)). For example, U.S. Pat. No. 4,714,680 issued Dec. 22, 1987, discloses a method of harvesting marrow from donors. Monoclonal antibodies that recognize a stage-specific antigen or immature human marrow cells are provided. These antibodies are useful in methods of isolating cell suspension from human blood and marrow that can be employed in bone marrow transplantation. Cell suspensions containing human pluripotent lympho-hematopoietic stem cells are also provided, as well as therapeutic methods employing the cell suspensions.

Several groups of investigators since 1990 have attempted to prepare more homogenous populations. For example, U.S. Pat. No. 5,087,570, issued Feb. 11, 1992, discloses how to isolate homogeneous mammalian hematopoietic stem cell compositions. Concentrated hematopoietic stem cell compositions were substantially free of differentiated or dedicated hematopoietic cells. The desired cells are obtained by subtraction of other cells having particular markers. The resulting composition may be used to provide for individual or groups of hematopoietic lineages, to reconstitute stem cells of the host, and to identify an assay for a wide variety of hematopoietic growth factors.

U.S. Pat. No. 5,633,426 issued May 27, 1997, is another example of the differentiation and production of hematopoietic cells. Chimeric immunocompromised mice are given human bone marrow of at least 4 weeks from the time of implantation. The bone marrow assumed the normal population of bone marrow except for erythrocytes. These mice with human bone marrow may be used to study the effect of various agents on the proliferation and differentiation of human hematopoietic cells.

U.S. Pat. No. 5,665,557 issued Sep. 9, 1997, relates to methods of obtaining concentrated hematopoietic stem cells by separating out an enriched fraction of cells expressing the marker CDw109. Methods of obtaining compositions enriched in hematopoietic megakaryocyte progenitor cells are also provided. Compositions enriched for stem cells and populations of cells obtained therefrom are also provided by the invention. Methods of use of the cells are also included.

U.S. Pat. No. 5,753,505 issued on Jun. 5, 1995, is yet another method of differentiation. Primordial tissue is introduced into immunodeficient hosts, where the primordial tissue develops and differentiates. The chimeric host allows for investigation of the processes and development of the xenogeneic tissue, testing for the effects of various agents on the growth and differentiation of the tissue, as well as identification of agents involved with the growth and differentiation.

U.S. Pat. No. 5,753,505 issued May 19, 1998, provides an isolated cellular composition in comprising greater than about 90% mammalian, non-tumor-derived, neuronal progenitor cells which express a neuron-specific marker and which can give rise to progeny which can differentiate into neuronal cells. Also provided are methods of treating neuronal disorders utilizing this cellular composition.

U.S. Pat. No. 5,759,793 issued Aug. 6, 1996, provides a method for both the positive and negative selection of at least one mammalian cell population from a mixture of cell populations utilizing a magnetically stabilized fluidized bed. One application of this method is the separation and purification of hematopoietic cells. Target cell populations include human stem cells.

U.S. Pat. No. 5,789,148 issued Aug. 4, 1998, discloses a kit, composition and method for cell separation. The kit includes a centrifugable container and an organosilanized silica particle-based cell separation suspension suitable for density gradient separation, containing a polylactam and sterilized by treatment with ionizing radiation. The composition includes a silanized silica particle-based suspension for cell separation that contains at least 0.05% of a polylactam, and preferably treated by ionizing radiation. Also disclosed is a method of isolating rare blood cells from a blood cell mixture.

Within the past several years, MSCs have been explored as vehicles for both cell therapy and gene therapy. The cells are relatively easy to isolate from the small aspirates of bone marrow that can be obtained under local anesthesia; they are also relatively easy to expand in culture and to transfect with exogenous genes. Prockop, D. J. *Science* 26: 71–74 (1997). Therefore, MSCs appear to have several advantages over hematopoietic stem cells (HMCs) for use in gene therapy. The isolation of adequate numbers of HSCs requires large volumes of marrow (1 liter or more), and the cells are difficult to expand in culture. (Prockop, D.J. (ibid.)).

There are several sources for bone marrow tissue, including the patient's own bone marrow, that of blood relatives or others with MHC matches, bone marrow banks, and umbilical cord blood banks. There are several patents that encompass this source. U.S. Pat. No. 5,476,997 issued May 17, 1994, discloses a method of producing human bone marrow equivalent. A human hematopoietic system is provided in an immunocompromised mammalian host, where the hematopoietic system is functional for extended periods of time. Particularly, human fetal liver tissue and human fetal thymus are introduced into a young immunocompromised mouse at a site supplied with a vascular system, whereby the fetal tissue results in formation of functional human bone marrow tissue.

A source of implantable neurons that is the most ethically controversial, is that of human fetal tissue. U.S. Pat. No. 5,690,927 issued Nov. 25, 1997, also utilizes human fetal tissue. Human fetal neuro-derived cell lines are implanted into host tissues. The methods allow for treatment of a variety of neurological disorders and other diseases. A preferred cell line is SVG.

U.S. Pat. No. 5,753,491 issued May 19, 1998, discloses methods for treating a host by implanting genetically unrelated cells in the host. More particularly, the present invention provides human fetal neuro-derived cell lines, and methods of treating a host by implantation of these immortalized human fetal neuro-derived cells into the host. One source is the mouse, which is included in the U.S. Pat. No. 5,580,777 issued Dec. 3, 1996. This patent features a method for the in vitro production of lines of immortalized neural precursor cells, including cell lines having neuronal and/or glial cell characteristics, comprises the step of infecting neuroepithelium or neural crest cells with a retroviral vector carrying a member of the myc family of oncogenes.

U.S. Pat. No. 5,753,506 issued May 19, 1998, reveals an in vitro procedure by which a homogeneous population of multipotential precursor cells from mammalian embryonic neuroepithelium (CNS stem cells) was expanded up to $10^9$ fold in culture while maintaining their multipotential capacity to differentiate into neurons, oligodendrocytes, and astrocytes. Chemical conditions are presented for expanding a large number of neurons from the stem cells. In addition, four factors—PDGF, CNTF, LIF, and T3—have been identified which, individually, generate significantly higher proportions of neurons, astrocytes, or oligodendrocytes. These procedures are intended to permit a large-scale preparation of the mammalian CNS stem cells, neurons, astrocytes, and oligodendrocytes. These cells are proposed as an important tool for many cell- and gene-based therapies for neurological disorders.

Another source of stem cells is that of primate embryonic stem cells. U.S. Pat. No. 5,843,780 issued Dec. 1, 1998, utilizes these stem cells. A purified preparation of stem cells is disclosed. This preparation is characterized by the following cell surface markers: SSEA-1 (−); SSEA-3 (+); TRA-1–60 (+); TRA-1–81 (+); and alkaline phosphatase (+). In one embodiment, the cells of the preparation have normal karyotypes and continue to proliferate in an undifferentiated state after continuous culture for eleven months. The embryonic stem cells lines are also described as retaining the ability to form trophoblasts and to differentiate into tissues derived from all three embryonic germ layers (endoderm, mesoderm and ectoderm). A method for isolating a primate embryonic stem cell line is also disclosed in the patent.

In summary, there is substantial evidence in both animal models and human patients that neural transplantation is a scientifically feasible and clinically promising approach to the treatment of neurodegenerative diseases and stroke as well as for repair of traumatic injuries to brain and spinal cord. Nevertheless, alternative cell sources and novel strategies for differentiation are needed to circumvent the numerous ethical and technical constraints that now limit the widespread use of neural transplantation.

SUMMARY OF DISCLOSURE

This invention provides a novel source of neuronal tissue that can be used for grafting into the patient's own brain or spinal cord (autografting). This invention thus bypasses the delicate issue of using pooled fetal tissue and also obviates the need for immunosuppression. This invention will also be used for allografting (transplantation of bone marrow-derived neuronal cells from one individual to another) and xenografting (transplantation of bone marrow-derived neuronal cells from one species to another). Simply stated, bone marrow cells can be induced to become neurons in vitro and in vivo. Neither the concept nor the technique has been previously reported or accomplished.

In one embodiment, there are disclosed non-fetal, non-tumorigenic, bone-marrow derived neuronal cells suitable for grafting into a mammal's brain or spinal cord.

In another embodiment, there is disclosed a novel method for obtaining neuron-like cells from bone marrow, said method comprising the steps of a) obtaining bone marrow cells; b) selecting for bone marrow stromal cells; and c) incubating the stromal cells with a differentiating agent, for a time sufficient to change the cell phenotype to neuronal. The method may include an additional step of separating out hematopoietic stem cells. The method of selecting bone marrow stromal cells may include placing the bone marrow cells and suitable culture medium in a plastic culture medium container, allowing the bone marrow stromal cells to adhere to the plastic, and removing the other cells by replacing the medium. The method also provides for using retinoic acid, growth factors, fetal neuronal cells or a combination thereof as the differentiating agent. The growth factors include BDNF, GDNF and NGF. Retinoic acid is 9-cis retinoic acid, all-transretinoic or a combination thereof.

A method for obtaining neurons for auto-transplant from an individual's own bone marrow, includes the steps of a) harvesting the bone marrow; b) selecting for bone marrow stromal cells; c) incubating the bone marrow stromal cells in a medium including a mitogen until there are sufficient cells for transplantation; d) incubating the stromal cells of step c) with a differentiating agent for a time sufficient to change the cell phenotype to neuronal and/or glial. The mitogen is EGF, PDGF or a combination thereof. The method may include an additional step of separating out hematopoietic stem cells. The method of selecting bone marrow stromal cells may include placing the bone marrow cells and suitable culture medium in a plastic culture medium container, allowing the bone marrow stromal cells to adhere to the plastic, and removing the other cells by replacing the medium. The differentiating agent is selected from retinoic acid, growth factors, fetal neuronal cells or a combination thereof. The growth factors are BDNF, GDNF and NGF, or a combination thereof. Retinoic acid is 9-cis retinoic acid, all-transretinoic or a combination thereof.

Also disclosed is a cell line of bone marrow stromal cells developed by an above method, such that the cells have the ability to migrate and localize to specific neuroanatomical regions where they differentiate into neuronal cells typical of the region and integrate in characteristic architectonic patterns.

Also disclosed is a kit for neuronal cell transplantation with a syringe suitable for obtaining bone marrow, a plastic flask with dehydrated culture medium; and bone marrow stem cell.

Also disclosed is a method of treating a neurodegenerative disorder including administering a sufficient quantity of the cells produced by an above method to an individual with said neurodegenerative disorder. Specific neurodegenerative disorders include Parkinson's Disease, Alzheimer's disease, ischemia, spinal cord damage, ataxia, and alcoholism.

Another embodiment is a method of screening for effects of substances on human neuronal cells. The method calls for providing a mammal with implanted human neuronal cells, said cells having migrated to at least one specific location in the mammal's brain; administering the mammal the substance; and observing the mammal for an effect of the substance.

BRIEF DESCRIPTION OF THE DRAWINGS

The file of this patent contains at least one drawing executed in color. Copies of this patent with color drawings are provided to the Patent and Trademark Office with payment of the necessary fee.

FIG. 1 is a bar graph. BMSC adherent to culture dishes were treated with EGF (10 ng/ml), RA (0.5 $\mu$M) or RA plus BDNF (10 ng/ml) for 7 days. Each bar represents the mean number ($\pm$SEM) of fibronectin immunoreactive cells per visual field (20×objective) determined in 20 fields per dish in 4 culture dishes. *=p<0.05, two-tailed t-test FIGS. 2A through 2F are photomicrographs of BMSC from lacZ mice that have been co-cultured with mouse fetal midbrain cells for 2 weeks in N5 medium supplemented with cis-9 retinoic acid (0.5 $\mu$M) and BDNF (10 ng/ml).

FIGS. 3A through 3F are photomicrographs, which illustrate the migration and integration of BMSC into rat midbrain. FIG. 3A (scale bar=500 $\mu$m) shows symmetrical distribution despite unilateral grafting into the striatum. FIG. 3B is a region of the paraventricular nucleus (scale bar=100 $\mu$m). None of the β-gal+cells are labeled with the red-brown stain (TH-ir). FIGS. 3A (Scale bar=500 $\mu$m), 3B (Scale bar=100 $\mu$m) and 3C (Scale bar=50 $\mu$m) depict cells doubly stained for β-gal and TH-ir. FIGS. 3D (Scale bar=50 $\mu$m)

and 3E (Scale bar=25 μm) illustrate sections from the red nucleus that have doubly stained for β-gal and NeuN-ir. FIG. 3F (Scale bar=25 μm) illustrates β-gal+cells from the red nucleus also doubly stained for MAP2-ir.

FIGS. 4A through 4F are photomicrographs of a section from rat cerebellar lobule illustrating laminar distribution of β-gal+cells in a distribution of Purkinje cells. β-gal+are co-labeled with calbindin immunoreactivity in FIGS. 4A, 4B, and 4C. (Scale bar=100 μm in 4A, 50 μm in 4B and 25 μm in 4C). FIG. 4D shows β-gal+Purkinje cells co-labeled with GAD-ir (Scale bar=50 μm). FIG. 4E illustrates dense MAP2-ir fibers enveloping β-gal+Purkinje cells (Scale bar=25 μm). FIG. 4F illustrates β-gal+cells co-labeled with NeuN-ir in the deep cerebellar nucleus (Scale bar=25 μm).

FIGS. 5A through 5D are photomicrographics showing the production of markers for fibronectin (FIG. 5A) and differentiated BMSC with nerve cell markers (FIGS. 5B, 5C and 5D).

FIG. 6 is a Western blot of the lysates of BMSC conditioned with four different treatments and labeled with GFAP-ir, nestin and NeuN. BDNF+RA+N5 induced the strongest expression of nerve cell markers while glial cell markers was most strongly expressed after N5 alone.

FIGS. 7A through 7F are photomicrographs of human BMSC which were co-cultured with fetal rat striatal cells in N5 formulation with BDNF+RA. These figures show that human BMSC (green labeled in FIGS. 7C and 7D and yellow in FIGS. 7E and 7F) can be induced to express neural markers NeuN (FIGS. 7A and 7E) and GFAP (FIGS. 7B and 7F).

FIG. 8 is a photomicrograph of rat brain, showing that mouse BMSC labeled with red PKH26 also express the neuron marker NeuN-ir (green fluorescence). In addition, the morphology of the doubly labeled cells is that of neurons.

FIG. 9 is a photomicrograph of rat brain, showing a doubly labelled glial cell. The red fluorescent tracer identifies it as derived from a BMSC, and the green fluorescence is due to GFAP-ir. Note the morphology is that of a glial cell.

DESCRIPTION OF THE PREFERRED EMBODIMENT

The ancient Chinese medical maxim "brain is a sea of marrow" (W. R. Morse, CHINESE MEDICINE, Paul Hoeber, Inc., New York City, 1938).) resonates with recent research findings regarding the capacity of a population of bone marrow cells to differentiate into neurons under experimental conditions.

In Western medicine, the existence of non-hematopoietic stem cells in bone marrow was suggested over 100 years ago, but the isolation and differentiation of marrow stromal cells into osteoblasts, chondroblasts, adipocytes and myoblasts was only recently demonstrated. D. J. Prockop, Science 276: 71–74 (1997). In the medical literature, non-hematopoietic precursors from bone marrow stroma have been referred to as colony-forming-unit fibroblasts, mesenchymal stem cells or bone marrow stromal cells (BMSC). Although BMSC can naturally be expected to be a source of surrounding tissue of bone, cartilage and fat, several recent reports demonstrate that these cells, under specific experimental conditions, can migrate and differentiate into muscle or glial cells. Systemic infusion of BMSC into irradiated 3-week-old mice has resulted in the appearance of progeny of the donor cells in a variety of non-hematopoietic tissues including the brain. R. F. Pereira, et al., Proc. Natl. Acad. Med. (USA) 95: 1142–1147 (1998). Transplantation of genetically-labeled bone marrow cells into immunodeficient mice has been reported to result in migration of marrow cells into a region of chemically-induced muscle degeneration. G. Ferrari, et al., Science 279: 1528–1530 (1998). These marrow-derived cells underwent myogenic differentiation and participated in the regeneration of the damaged muscle fibers. Moreover, infusion of human BMSC into rat striatum resulted in engrafting, migration and survival of cells. S. A. Azizi, et al., Proc. Nat. Acad. Sci. (USA) 95: 3908–3913 (1998). After engraftment, these cells lost typical BMSC markers, such as immunoreactivity to antibodies against collagen and fibronectin. BMSC developed many of the characteristics of astrocytes, and their engraftment and migration markedly contrasts with fibroblasts that continue to produce collagen and undergo gliosis after implantation. Following transplantation of bone marrow into lethally irradiated rats, bone marrow-derived cells were found to replace between 60 and 80% of the host macrophages in sensory and autonomic ganglia as well as in peripheral nerves. K. Vass, W. F. Hickey, R. E. Schmidt, H. Lassman, Laboratory Investigation 69: 275–282 (1993). In that study, no attempt was made to determine whether marrow cells differentiated into glial or neuronal cells.

Our laboratory has recently succeeded in differentiating BMSC into a neuron-like phenotype, using a combination of retinoic acid, growth factors, and fetal neuronal environments. Moreover, we have grafted BMSC into denervated rat striatum and have found that BMSC migrate into specific neuroanatomical regions where they differentiate into cells which expressing markers of neighboring cells. In those regions, the cells integrate in to characteristic arthitectonic patterns.

Definitions:

"Neuronal cells" are those having at least an indication of neuronal phenotype, such as staining for one or more neuronal markers. Examples of neuronal markers include, but are not limited to, neuron-specific nuclear protein, tyrosine hydroxylase, microtubule associated protein, nestin and calbindin.

"Non-tumorigenic" refers to the fact that the cells do not give rise to a neoplasm or tumor.

As used herein, "non-fetal" refers to the fact that the source has been born. It does not exclude umbilical cord blood.

Selecting for bone marrow stromal cells can be done in a number of ways. Classically, the stromal cells are disaggregated and cultured inside a plastic container. The stromal cells are separated by their survival in specific media and adherence to the plastic.

Bone-marrow cells can be induced to adopt a number of different neuronal phenotypes, as proven below by in vitro and in vivo observations. Additional in vitro differentiation techniques can be adapted through the use of various cell growth factors and co-culturing techniques known in the art. Besides co-culturing with fetal mesencephalic or striatal cells (as successfully demonstrated below), a variety of other cells can be used, including but not limited to accessory cells, Sertoli cells and cells from other portions of the fetal and mature central nervous system.

General Methods

Standard molecular biology techniques known in the art and not specifically described are generally followed as in Sambrook et al., MOLECULAR CLONING: A LABORATORY MANUAL, Cold Springs Harbor Laboratory, N.Y. (1989, 1992), and in Ausubel et al., CURRENT PROTOCOLS IN MOLECULAR BIOLOGY, John Wiley and Sons, Baltimore, Md. (1989). Polymerase chain reaction (PCR) is carried out generally as in *PCR PROTOCOLS: A GUIDE TO METHODS AND APPLICATIONS*, Academic Press, San Diego, Calif. (1990). Reactions and manipulations involving other nucleic acid techniques, unless stated otherwise, are performed as generally described in Sambrook, et al., 1989, *MOLECULAR CLONING: A LABORATORY MANUAL*, Cold Springs Harbor Laboratory Press, and methodology as set forth in U.S. Pat. Nos. 4,666,828; 4,683,202; 4,801,531; 5,192,659; and 5,272,057 and incorporated herein by reference. In-situ PCR in combination with Flow Cytometry can be used for detection of cells containing specific DNA and mRNA sequences (Testoni et al. *Blood* 87:3822 (1996)).

Standard methods in immunology known in the art and not specifically described are generally followed as in Stites et al. (eds), BASIC AND CLINICAL IMMUNOLOGY, 8$^{th}$ Ed., Appleton & Lange, Norwalk, Conn. (1994); and Mishell and Shigi (eds), SELECTED METHODS IN CELLULAR IMMUNOLOGY, W. H. Freeman and Co., New York (1980).

Immunoassays

In general immunoassays are employed to assess a specimen such as for cell surface markers or the like. Immunocytochemical assays are well known to those skilled in the art. Both polyclonal and monoclonal antibodies can be used in the assays. Where appropriate other immunoassays, such as enzyme-linked immunosorbent assays (ELISAs) and radioimmunoassays (RIA), can be used as are known to those in the art. Available immunoassays are extensively described in the patent and scientific literature. See, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521 as well as Sambrook et al., *MOLECULAR CLONING: A LABORATORY MANUAL*, Cold Springs Harbor, N.Y. (1989).

Antibody Production

Antibodies may be monoclonal, polyclonal or recombinant. Conveniently, the antibodies may be prepared against the immunogen or portion thereof, for example, a synthetic peptide based on the sequence, or prepared recombinantly by cloning techniques or the natural gene product and/or portions thereof may be isolated and used as the immunogen.

Immunogens can be used to produce antibodies by standard antibody production technology well known to those skilled in the art as described generally in Harlow and Lane, *ANTIBODIES: A LABORATORY MANUAL*, Cold Spring Harbor Laboratory, Cold Springs Harbor, N.Y. (1988) and Borrebaeck, *ANTIBODY ENGINEERING—A PRACTICAL GUIDE*, W. H. Freeman and Co. (1992). Antibody fragments may also be prepared from the antibodies and include Fab and F(ab')$_2$ by methods known to those skilled in the art.

For producing polyclonal antibodies a host, such as a rabbit or goat, is immunized with the immunogen or immunogen fragment, generally with an adjuvant and, if necessary, coupled to a carrier; antibodies to the immunogen are collected from the serum. Further, the polyclonal antibody can be absorbed such that it is monospecific. That is, the serum can be exposed to related inimunogens so that cross-reactive antibodies are removed from the serum rendering it monospecific.

For producing monoclonal antibodies, an appropriate donor is hyperimmunized with the immunogen, generally a mouse, and splenic antibody-producing cells are isolated. These cells are fused to immortal cells, such as myeloma cells, to provide a fused cell hybrid which is immortal and secretes the required antibody. The cells are then cultured, and the monoclonal antibodies harvested i from the culture media.

For producing recombinant antibodies, messenger RNA from antibody-producing B-lymphocytes of animals or hybridoma is reverse-transcribed to obtain complementary DNAs (cDNAs). Antibody cDNA, which can be full or partial length, is amplified and cloned into a phage or a plasmid. The cDNA can be a partial length of heavy and light chain cDNA, separated or connected by a linker. The antibody, or antibody fragment, is expressed using a suitable expression system. Antibody cDNA can also be obtained by screening pertinent expression libraries.

The antibody can be bound to a solid support substrate or conjugated with a detectable moiety or be both bound and conjugated as is well known in the art. (For a general discussion of conjugation of fluorescent or enzymatic moieties see Johnstone & Thorpe, *IMMUNOCYTOCHEMISTRY IN PRACTICE*, Blackwell Scientific Publications, Oxford (1982)). The binding of antibodies to a solid support substrate is also well known in the art. (see for a general discussion Harlow & Lane ANTIBODIES: A LABORATORY MANUAL, Cold Spring Harbor Laboratory Publications, New York, 1988 and Borrebaeck, *ANTIBODY ENGINEERING—A PRACTICAL GUIDE*, W. H. Freeman and Co. (1992)). The detectable moieties contemplated with the present invention can include, but are not limited to, fluorescent, metallic, enzymatic and radioactive markers. Examples include biotin, gold, ferritin, alkaline phosphates, â-galactosidase, peroxidase, urease, fluorescein, rhodamine, tritium, $^{14}$C, iodination and green fluorescent protein.

Gene Therapy

Gene therapy as used herein refers to the transfer of genetic material (e.g., DNA or RNA) of interest into a host to treat or prevent a genetic or acquired disease or condition. The genetic material of interest encodes a product (e.g., a protein, polypeptide, peptide, functional RNA, antisense) whose in vivo production is desired. For example, the genetic material of interest encodes a hormone, receptor, enzyme, polypeptide or peptide of therapeutic value. Alternatively, the genetic material of interest encodes a suicide gene. For a review see "Gene Therapy" in *ADVANCES IN PHARMACOLOGY* 40, Academic Press, San Diego, Calif., 1997.

Delivery of Cells

The cells of the present invention are administered and dosed in accordance with good medical practice, taking into account the clinical condition of the individual patient, the site and method of administration, scheduling of administration, patient age, sex, body weight and other factors known to medical practitioners. The pharmaceutically "effective amount" for purposes herein is thus determined by such considerations as are known in the art. The amount must be effective to achieve improvement, including but not limited to improved survival rate or more rapid recovery, or improvement or elimination of symptoms and other indicators as are selected as appropriate measures by those skilled in the art.

In the method of the present invention, the cells of the present invention can be administered in various ways as would be appropriate to implant in the central nervous system, including but not limited to parenteral administration, intrathecal administration, intraventricular administration and intranigral administration.

EXAMPLES

Example 1

In Vitro Differentiation

Bone marrow was obtained from either mouse femurs or from human bone marrow aspirates. Human bone marrow was diluted 1:1 with Dulbecco's Minimal Essential Media (DMEM), (GIBCO/BRL) and 10% fetal bovine serum (FBS) and centrifuged through a density gradient (Ficoll-Paque Plus, 1.077 g/ml, Pharmacia) for 30 min at 1,000 g. The supernatant and interface were combined, diluted to approximately 20 ml with MEM with 10% fetal calf serum (FCS) and plated in polyethylene-imine coated plastic flasks. Mouse bone marrow was placed in 10 ml PBS and 5% bovine albumin. Cells were washed in this medium and centrifuged at 2000 rpm for 5 min. Cells were resuspended in growth medium consisting of DMEM supplemented with 2mM glutamine, 0.001% β-mercaptoethanol, non-essential amino acids and 10% horse serum. The cells were incubated in the flasks for two days after which non-adherent cells were removed by replacing the medium. After the cultures reached confluency, the cells were lifted by applying trypsin (0.25%) and 1 mM EDTA and incubating at 37° C. for 3–4 min. Some of the cells were frozen for later use. To expand the cell population, other cells were replated after 1:2 or 1:3 dilution with the addition of a mitogen such as epidermal growth factor (EGF) at a concentration of 10 ng/ml or platelet-derived growth factor (PDGF) at a concentration of 5 ng/ml. This procedure has been repeated for 3–5 passages.

Differentiation of BMSC cells into neuron-like cells was the next step. Cells which have been removed from the plastic flask bottom as described above were replated in 35 mm culture dishes in the presence of a neuronal growth medium (N5) (Kaufinan & Barrett, *Science* 220:1394, 1983), supplemented with 5% BSA, 1% FBS, transferrin (100 g/ml), putrescine (60 M), insulin (25 g/ml), progesterone (0.02 M), selenium (0.03 M), 9-cis retinoic acid or all-trans retinoic acid (0.5 M), and any one of several neuronal growth factors at a concentration of 1–10 ng/ml. The growth factors tested were brain-derived growth factor (BDNF), glial-derived neurotrophic factor (GDNF) and nerve growth factor (NGF). After 7–14 days, a small proportion of BMSC changed morphology and expressed proteins such as nestin (a marker of cells destined to become neural cells), neuron-specific nuclear antigen (NeuN), tyrosine hydroxylase (TH) and glial fibrillary acidic protein (GFAP). As many as 4% of the cells developed a neuron-like or glial cell morphology when visualized immunohistochemically. These cells had not differentiated into "dendritic cells", as evidenced by the lack of staining for CD40.

Staining Characteristics of BMSC-Derived Cells

|  | NeuN | GFAP | TH | CD40 |
| --- | --- | --- | --- | --- |
| BDNF | +++ | + | ++ | − |
| GDNF | ++ | + | + | − |
| NGF | + | + | + | − |

Example 2

Bone marrow cells were induced to become neuron-like cells in vitro employing methods similar to those used to promote differentiation of embryonic stem (ES) cells. J. Dinsmore, et al., *Cell Transplantation* 5:131–143 (1996). Bone marrow was obtained from adult mice and divided into two fractions using magnetic cell sorting. First, bone marrow cells were collected from mouse femur and tibias by flushing the shaft with buffer (PBS supplemented with 0.5% BSA, pH 7.2) using a syringe with a #26 G needle. Cells were disaggregated by gentle pipetting several times. Cells were passed through 30 μm nylon mesh to remove remaining clumps of tissue. Cells were washed by adding buffer, centrifuging for 10 min at 200Xg and removing supernatant. The cell pellet was resuspended in 800 μL of buffer for each $10^8$ cells. With a magnetic cell sorting kit (Milteny Biotec, Inc, Auburn Tex.), hematopoietic bone marrow cells were labeled with Sca1+microbeads. The labeled bone marrow cells were placed on an MS+column for positive selection of Sca1+cells.

Specifically, 200 μL of Sca1 Multi-sort microbeads was added per $10^8$ total cells, mixed and incubated for 15 min at 6–12° C. One fraction was enriched with cells bearing the marker for mouse hematopoietic stem cell antigen (Sca1), and the second fraction was comprised of all other marrow cells (including the BMSC fraction). Cells were washed by adding 5–10× the labeling volume of buffer and centrifuged for 10 min at 200×g, and supernatant was removed. The cell pellet was resuspended in 500 μL buffer. The MS+/RS+ column was washed with 500 μL of buffer. The cell suspension was applied to the column and the negative cells passed through. The column was then rinsed with 500 μL of buffer three times. The column was removed from the separator (which contains the magnet), and placed on a suitable collection tube. One ml of buffer was pipetted onto the column and the positive fraction was flushed out with the plunger provided with the column. Sca1-labeled cells were placed in 10 ml PBS and 5% BSA. Cells were washed in this medium and centrifuged (2000 rpm for 5 min). Cells were resuspended in growth medium consisting of DMEM supplemented with 2 mM glutamine, 0.001% β-mercaptoethanol, non-essential amino acids, and 10% horse serum. The cells were incubated in polyethylene flasks for 2 days, and non-adherent cells were removed by replacing the medium. After the cultures reached confluency, the cells were loosened by incubation with trypsin (0.25%) and 1 mM EDTA at 37 C for 3–4 min. They were then frozen for later use or replated after 1:2 or 1:3 dilution with the addition of Epidermal Growth Factor (EGF), 10 ng/ml. The population of cells that adhered tightly to the bottom of the culture flasks appeared primarily fibroblastic. The majority of these cells stained with antibodies to fibronectin. These cells have been referred to as either mesenchymal stem cells, because of their mesenchymal or fibroblastic appearance, or as bone marrow stromal cells (BMSC) because they appear to arise from the complex array of supporting structures found in the marrow. D. J. Prockop, *Science* 276: 71–74 (1997).

Preliminary findings in our laboratory failed to find evidence for dendritic cells in BMSC cultured with retinoic acid (RA) and growth factor (BDNF, GDNF or NGF) (Example 1). Moreover, the number of fibronectin immunoreactive cells decreased as a function of treatment with RA and it growth factor, demonstrating that retinoic acid and growth factor induced differentiation of BMSC away from a fibroblastic phenotype (See FIG. 1).

To determine if the cellular environment influences differentiation of these cells, BMSC were co-cultured with fetal mesencephalic cells. The BMSC were obtained from transgenic lacZ mice (Jackson Labs.) which express β-galactosidase (β-gal) in bone marrow cells. The lacZ BMSC were plated in equal proportion with fetal mesencephalic cells, prepared as previously described (J. R. Sanchez-Ramos, P. Michel, W. J. Weiner, F. Hefti, Journal of Neurochemistry 50: 1934–1944 (1988)) from mice of another strain (C57 bl6; Jackson Labs) in culture medium containing cis-9 retinoic acid (0.5 μM) and BDNF (10 ng/ml). After 2 wks, cultures were fixed and processed for β-gal histochemistry and immunocytochemistry for neuronal markers. β-gal+from lacZ BMSC were clearly identified by a blue reaction product visualized under bright field microscopy (FIGS. 2A, 2C and 2E), and neurons were identified by neuron-specific nuclear protein immunoreactivity (NeuN-ir) using a fluorescein-linked secondary antibody. FIGS. 2B, 2D and 2F are the corresponding NeuN-ir images of 2A, 2C and 2E, respectively. In FIG. 2A, cells numbered 1, 2 and 3 are β-gal+cells and are co-labeled with Neu-ir, as shown in FIG. 2B. Many spindle-shaped cells with neuron-like processes exhibited both β-gal staining and NeuN-ir but the neurons from the fetal mesencephalic cells were distinguishable because they were larger and not β-gal+. For example, in FIG. 2E, cell numbered 1 does not show β-gal staining does show Neur-N-ir in FIG. 2F, and hence is a fetal mesencephalic neuron. In contrast, in FIG. 2E, cells numbered 2 through 6 were β-gal+BMSC-derived cells which exhibit NeuN-ir (FIG. 2F) and thus have become neuron-like cells. These results indicated that neuronal environment as well as the appropriate differentiation/growth factors induced transformation of the majority of BMSC into a neuronal phenotype.

Example 3

In Vivo Differentiation

To determine whether differentiation of BMSC cells into neurons would occur in vivo, BMSC from lacZ mice were grafted into denervated or normal rat striatum. Prior to grafting, BMSC were treated for 2 days with cis-9 retinoic acid (0.5 μM) and BDNF (10 ng/ml). Three weeks prior to grafting, the graft site of the caudate/putamen of rats was treated with unilateral intranigral injections of 6-hydroxydopamine (6-OH DA). A single injection of 6-OH DA (Sigma; 2.5 μL, 3.6 μg/μL for a total dose of 9 μg in 0.2% ascorbic acid) was made into the right ascending mesostriatal dopaminergic system (4.4 mm posterior to bregma, −1.2 mm laterally and −7.8 mm ventral to dura with the toothbar set at −2.4 mm). The 6-OH DA was delivered at a rate of 1 μL/min. The syringes were held in place for an additional 5 min before slow withdrawal.

BMSC suspension aliquots were deposited in the striatum along a single needle tract on the same side as the 6-OH DA nigral lesion in 6 animals. The rats were anesthetized with Na pentobarbital and placed in a stereotaxic frame. Cell suspension aliquots were deposited into two separate sites in the striatum along a single needle tract. The coordinates for the injections were 1.2 mm anterior to bregma, +2.7 mm laterally, and −5.2 mm and −4.7 mm ventral to dura with the toothbar set at zero. Each injection of 2 μl was delivered at a rate of 1 μl/min. The number of stem cells injected into the striatum was 20,000 cells/μl for a total of 80,000 cells. In two rats, a second injection of cells was made into the striatum in the unlesioned side resulting in a total of 160,000 cells per rat.

One, two and three months after grafting, pairs of animals were sacrificed, perfused with heparinized saline and phosphate-buffered paraformaldehyde. Serial cryostat sections 30 μm thick were cut through the entire length of the brain. Sections were first stained for β-gal activity followed by immunohistochemical processing with antibodies to neuron-specific nuclear protein (NeuN), several blocking agents to decrease non-specific immunolabeling and a second antibody coupled with peroxidase and a red-brown chromagen (Histomouse Kit, Zymed). Other neuronal markers assessed immunohistochemically included tyrosine hydroxylase (TH), glutamate decarboxylase (GAD), calbindin, and microtubule associated protein (MAP2).

The animals behaved and ambulated normally up to the time of sacrifice. Since this experiment was specifically designed to determine whether grafts survived and differentiated, the animals were not challenged with apomorphine or amphetamine to determine whether the 6-OH DA lesion and subsequent grafting altered rotational behavior. Examination of brain tissue sections revealed BMSC-derived β-gal+cells in multiple brain regions distant from the site of implantation in the corpus striatum. Orderly accumulation of β-gal+cells was found in the following specific brain regions: mitral cell zone of the olfactory bulb, paraventricular and supraoptic nuclei of hypothalamus, hippocampus, habenula, oculomotor nucleus, red nucleus, s. nigra, abducens, facial and hyoglossal cranial nerve nuclei, inferior olive of medulla, ventral horn of the spinal cord and the cerebellar Purkinje cell layer. The distribution of β-gal+ cells was bilateral and nearly symmetrical in all regions except the s. nigra, in which the unlesioned side exhibited a greater number of β-gal+cells (FIG. 3A, and Table I). The β-gal+BMSC cells were distributed in the cerebellum in a laminar pattern identical to that of Purkinje cells (FIGS. 4A, 4B, 4C). A similar, though less dense laminar distribution of BMSC was seen in the mitral cell layer of the olfactory bulb. Cerebral cortex and corpus striatum, even at the site of grafting, did not accumulate significant numbers of β-gal+ cells, although these cells were commonly seen in capillary channels in those regions.

The BMSC β-gal+cells assumed multiple phenotypes including epithelial-like cuboidal cells in choroid plexus, small oligodendroglial-like cells in optic chiasm and subcortical white matter, large neuron-like cells in red nucleus, s. nigra, and in brainstem motor nuclei. The cerebellar β-gal+cells, like true Purkinje cells, expressed calbindin (FIGS. 4A, 4B and 4C) but did not express the neuronal marker NeuN. Interestingly, normal (non-β-gal+) Purkinje cells also do not express NeuN. Many β-gal+Purkinje cells were also co-labeled with GAD-ir (FIG. 4D). GAD is a marker for γ-aminobutyric acid (GABA), which is normally synthesized in Purkinje cells and released in the deep cerebellar nuclei. GABA is also the neurotransmitter utilized by local circuit neurons in the cerebellar cortex. Deep cerebellar nuclei also contained β-gal+cells, many of which were co-

TABLE I

Cell Counts in Midbrain Regions

| Midbrain Regions | Total cells co-labeled with NeuN-ir and β-gal | Total β-gal cells in region | % of β-gal cells labeled with NeuN-ir |
|---|---|---|---|
| 1 Month After Grafting BMSC (mean of counts from 2 rats) | | | |
| Red nucleus (R) | 3502 | 3938 | 88.9 |
| Red nucleus (L) | 3405 | 4410 | 77.2 |
| IIIrd n. nucleus (R) | 575 | 696 | 82.6 |
| IIIrd n. nucleus (L) | 494 | 769 | 64.2 |
| S. nigra (R) | 1534 | 1907 | 80.4 |
| S. nigra (L) | 2326 | 3347 | 69.5 |
| 3 Months after grafting (mean of counts from 2 rats) | | | |
| Red nucleus (R) | 4658 | 6092 | 76.4 |
| Red nucleus (L) | 4535 | 6171 | 73.5 |
| IIIrd n. nucleus (R) | 554 | 944 | 58.6 |
| IIIrd n. nucleus (L) | 686 | 1056 | 64.9 |
| S. nigra (R)** | 0 | 0 | 0 |
| S. nigra (L)** | 3745 | 4372 | 85.6 |
| VTA (R)** | 0 | 0 | 0 |
| VTA (L)** | 3459 | 6918 | 50.0 |

**neuronal marker in these regions was tyrosine hydroxylase (TH). Only the left (unlesioned) side contained BMSC-derived cells Stereologic counts of β-gal+cells (total and co-labeled with neuronal marker) in midbrain regions were determined in four rats, each of which was previously lesioned with 6-OH-DA injected into the right s. nigra followed by grafting of BMSC 3 weeks later into the right corpus striatum. Two rats were sacrificed 1 month and 2 rats sacrificed 3 months after grafting. Counts of TH-ir cells in the s. nigra and ventral tegmental area (VTA) was determined in only one animal. labeled with NeuN-ir (FIG. 4F). In the hippocampus a faint β-gal+staining of cells was noted, but these cells did not appear to express NeuN-ir.

The β-gal+cells with neuronal phenotype in the red nucleus were enmeshed in MAP-2 immunoreactive fibers (FIG. 3F). It was not possible to determine with light microscopy whether these fibers were efferents from or afferents to β-gal+cells. Similarly, the β-gal+cells in the Purkinje cell layer of the cerebellum appeared to be enmeshed in MAP-2-ir fibers (FIG. 4E) giving the impression that these cells had integrated into the neuronal circuitry of the cerebellum. Lack of immunocytochemical staining for fibronectin, a marker of bone marrow stromal cells within the marrow, indicated loss of native BMSC phenotype in the regions of site-specific differentiation at one and three months after grafting.

The total number of β-gal+cells and the proportion of β-gal+cells that expressed the neuronal marker NeuN were estimated using stereologic techniques in three discrete nuclei of the midbrain (red nucleus, oculomotor nuclei and the s. nigra each) in 4 animals (See Table 1). Estimates of BMSC-derived neurons was determined using the Optical Disector method in 30 1m cryopreserved sections. BMSC-derived (β-gal+) cells were directly counted in a small number of sections at predetermined uniform intervals for the entire set of sections encompassing the red nucleus, s. nigra and oculomotor nucleus. Within each section to be counted, the field of view was focused at the top of the section using a 40X objective. The focus was then shifted through the section, and the number of BMSC-derived neuronal profiles in focus at the top (height of dissector=9.25 $\mu$m) were counted. The total lacZ cell count and the total double labeled cells (NeuN+lacZ) in each region was determined using the calculation: $N=N_v \times V$ (ref)=$\Sigma Q/(\Sigma P \times v$ (dis))$\times V$ (ref); where $\Sigma Q$ is the total number of neurons counted in all dissectors in the reference volume, and v(dis) is the volume of the disector which is equal to the area of the test frame multiplied by the height of the dissector (9.25 $\mu$m) which is the distance between the focal planes.

With the exception of the s. nigra and ventral tegmental area (VTA), the numbers of β-gal+cells in all regions were distributed symmetrically, despite a unilateral right nigral lesion and ipsilateral grafting into the striatum. The total number of β-gal+cells in s. nigra and VTA on the right side was lower than on the unlesioned left side at both one and three months after grafting. The percentage of β-gal+cells that co-expressed NeuN-ir ranged from 58.6% in the oculomotor nucleus to 89% in the red nucleus. Estimates of β-gal+cells co-labeled with TH-ir in the s. nigra and VTA were made in only one animal 3 months after grafting. The percentage of β-gal+cells that co-expressed TH in the s. nigra was 12.9% on the side of the 6-OH DA lesion and 69.7% on the unlesioned side. A similar pattern was seen in the VTA where the percentage of β-gal+cells co-labeled with TH was 19.8% on the side of the lesion and 50% on the unlesioned side. Estimates of the total number of cells in the midbrain were increased slightly at three months when compared to cell counts one month after grafting. The sum of all β-gal+cells in the midbrain regions counted at 1 month averaged 15,067 which represents 18% of the original 80,000 cells grafted into the striatum. At 3 months the total number of β-gal+cells in the midbrain regions averaged 18,635 (23% of the total grafted). The slight increase in numbers of β-gal+cells is unlikely to represent continued cell division since proliferating cell nuclear antigen immunoreactivity (PCNA-ir) was not detected in those regions where BMSC had assumed neuronal morphology. Analysis of the two animals that had received bilateral grafts revealed similar bilateral distributions and patterns of differentiation of BMSC two months after grafting. However, stereologic estimates were not done in these animals.

These results indicate that our treated BMSC contain pluripotential cells which differentiate into neurons, as indicated by several neuronal markers, morphological characteristics, and integration into specific architectonic layers or regions. We provided a stimulus (lesion of the nigro-striatal system) with which we intended to induce BMSC differentiation. However, the nigral lesion had a negative influence on local engraftment at the site of implantation. Instead, the β-gal+BMSC migrated extensively and differentiated in a site-dependent bilateral symmetrical distribution in all parts of the brain, with the exception of the s. nigra and VTA. At the site of the 6-OH DA nigral a lesion, there were fewer β-gal+BMSCs and a smaller proportion of them co-expressed TH when compared to the unlesioned side. This may have been affected by the age of the lesion (three weeks). Ordinarily, there is an optimal time for grafting cells into models of neurodegeneration and hypoxia-ischemia. Other neural "stem-like" cells grafted into brain have been shown to migrate preferentially to the site of ischemia in the injured hemisphere of the hypoxic-ischemic rat model, but optimal migration and engraftment was achieved when cells were implanted 3–7 days after the lesion. E. Y. Snyder et al., *ADVANCES IN NEUROLOGY VOL. 72: NEURONAL REGENERATION, REORGANIZATION, AND REPAIR.* (ed. F. J. Seil) Lippincott-Raven, Philadelphia, 1997.

Since the lesion was unlikely to have affected site-dependent differentiation in regions remote from the nigro-striatal system, the most likely explanation for the neurotropism or affinity of BMSC for specific neuronal populations was due to pre-treating BMSC with retinoic acid and BDNF prior to grafting. In contrast, it has been shown that untreated human BMSC transplanted into normal rat striatum have not differentially distributed nor differentiated by site, despite their widespread migration. S. A. Azizi, et al., *Proc. Nat. Acad. Sci. (USA)* 95: 3908–3913 (1998).

Not wishing to be bound by a theory, we nevertheless propose that pretreating BMSC with retinoic acid and BDNF induces expression of cell surface proteins or receptors with an affinity for corresponding trophic factors, cytokines or cell adhesion molecules normally produced by specific neuronal populations. This appears to be a useful model for studying the mechanism for the affinity of BMSC for specific brain regions. This affinity of pretreated BMSC for specific brain regions will permit targeting of neuronal populations for cellular therapies ranging from gene therapeutics to neural reconstruction in neurodegenerative diseases, stroke and trauma.

To be sure that the β-gal+cells are truly derived from BMSC, two other experiments were undertaken using BMSC labeled with other markers (Examples 7 and 8 below). This was necessary because some populations of normal ungrafted rat neurons express an endogenous β-galactosidase activity. With the presence of several other markers of mouse BMSC, we determined that the β-gal+cell were indeed derived from mouse and were not endogenous rat neurons.

Example 4

Ataxia Treatment

"Wobbler" mice (JAX labs) express a mutation in which the Purkinje cells of the cerebellum degenerate rapidly at 3 to 4 weeks of age. The loss of Purkinje cells appears to be the predominant effect of the mutation, and no other neurons degenerate other than mitral cells of the olfactory bulb and a few thalamic neurons. The loss of Purkinje cells correlates to the beginning of an ataxic "wobbly" gait which persists for life but which does not otherwise affect the health of the animals.

Pre-conditioned BMSC (as described above) are grafted into the brain of these animals at age 6 weeks. A total of 12 mutant animals and 12 normal animals are studied for each experiment. Half of the animals receive pre-conditioned BMSC from LacZ mice and half undergo sham surgery. Although the aim is to replace cerebellar Purkinje cells, the graft is placed in the striatum since we have demonstrated (Example 3) that cerebellum appears to be a preferred region for migration and site-specific differentiation into Purkinje-like neurons. Alternative graft sites are injection into the lateral ventricle and directly into the cerebellum, carefully so as to avoid inducing traumatic ataxia.

To determine whether the grafts result in functional improvement of the neurologic deficit, the pre-surgical baseline spontaneous gait are quantified by recording the inked paw prints left on a narrow 36 inch-long strip of paper on the bottom of an enclosed runway (36" long, 3" wide and 6" high). In addition, performance on a balance beam is measured (ability and time required to cross a rod suspended between two platforms). These measurements of locomotor activity and coordination are done in both the mutant mice and in the control group of normal mice with the same genetic background at the following time points: 1 week before surgery, and 1 week, 1 month, 2 months and 3months after surgery.

At a time point when there is significant improvement in locomotor activity and coordination, the animals are sacrificed, and the brains are examined for the distribution and degree of differentiation of the grafted BMSC. The BMSC origin of the cells is determined by β-gal staining. The marker for Purkinje cells is calbindin immunoreactivity. The proportion of β-gal+cells which are co-labeled with calbindin are determined using stereologic technique.

Example 5

Differentiation of Bone Marrow Cells (BMSC) In Vitro

To briefly summarize, BMSC were separated from whole bone marrow of the mouse, calf and humans. BMSC cultures were incubated with a) epidermal growth factor (EGF), b) Retinoic acid (RA), c) N5 neuronal medium and d) brain-derived neurotrophic factor (BDNF) plus RA.

BMSC were isolated from residual bone marrow material (bone chips with adherent stromal cells, fatty tissue and debris) which was retained on the nylon mesh filters routinely used in filtering freshly procured human marrow to be used for bone marrow transplantation. The filtrate contains the bulk of the bone marrow hematopoietic elements that is then processed for human bone marrow replacement. We use the filters that were usually discarded. The filters were back washed five times with PBS. The PBS solution was centrifuged to deposit the heavier bone chips. The supernatant was resuspended in culture medium and plated in tissue culture flasks (as in Example 1). BMSC were separated by their adherence to plastic culture flasks, whereas the smaller hematopoietic stem cells remained suspended in the media and were removed when the culture media was replaced with fresh media. Human bone marrow fraction for plating was diluted 1:1 with Dulbecco's Minimal Essential Media (DMEM, GIBCO/BRL) and 10% FBS, centrifuged through a density gradient (Ficoll-Paque Plus, 1.077 g/ml, Pharmacia) for 30 min at 1,000×g. The supernatant and interface were combined, diluted to approximately 20 ml with MEM with 10% fetal calf serum (FCS), and plated in polyethylene-imine coated plastic flasks.

Mouse bone marrow was placed in 10 ml PBS and 5% BSA. Cells were washed in this medium, centrifuged (2000 rpm for 5 min). Cells were resuspended in growth medium consisting of DMEM supplemented with 2 mM glutamine, 0.001% β-mercaptoethanol, non-essential amino acids, and 10% horse serum. The cells were incubated in the flasks for 2 days and non-adherent cells were removed by replacing the medium. After the cultures reach confluency, the cells were lifted by incubation with trypsin (0.25%) and 1 mM EDTA at 37° C. for 3–4 min. They were then frozen for later use or replated after 1:2 or 1:3 dilution with the addition of Epidermal Growth Factor (EGF), 10 ng/ml or Platelet-Derived Growth Factor (PDGF) 5 ng/ml. This procedure can be repeated for 3–5 passages.

Human whole bone marrow cells were allowed to adhere to the culture flask bottom for 2 days, and after removal from the flasks, were replated in medium containing the mitogen, epidermal growth factor (EGF). This resulted in proliferation of cells, without significant induction of differentiation. Cells were then removed from the flask bottom and replated (or frozen for later use) in 35 mm culture dishes in the presence of a neuronal growth medium (N5) supplemented with fetal calf serum (FCS) 10%, retinoic acid (RA) and one of several growth factors (BDNF, GDNF or NGF). The usual marrow stromal cells were rich in fibronectin (FIG. 5A). After 7 to 14 days, a small proportion (<2%) of the human BMSC developed a distinctly neuron-like phenotype and markers. Immunocytochemical analysis of cultures revealed the presence of nestin-ir cells (FIG. 5B), NeuN-ir cells (FIG. 5C) and GFAP-ir cells (FIG. 5D). BMSC incubated with RA and BDNF resulted in expression of the neuronal marker NeuN while the amount of fibronectin expressed was decreased compared to cultures conditioned with EGF alone.

After 7 days, expressions of neuronal markers (Nestin, Neuron Specific Nuclear protein or NeuN and GFAP) and a bone marrow stromal cell marker (fibronectin) were analyzed by Western blot analysis and immunocytochemistry (FIG. 6). For the Western blot analysis, cultures were washed 3 times in cold PBS, scraped into ice-cold PBS, and lysed in an ice-cold lysis buffer containing 20 nM Tris/HCl (pH=8.0), 0.2 mM EDTA, 3% Nonidet P-40, 2 mM orthovanadate, 50 mM NaF, 10 mM sodium pyrophosphate, 100 mM NaCl, and 10 μg each of aprotinin and leupeptin per ml. After incubation on ice for 10 min, the samples were centrifuged at 14,000×g for 15 min and the supernatants were collected. An aliquot was removed for total protein estimation (Bio-Rad assay). An aliquot corresponding to 30 μg of total protein of each sample was separated by SDA/PAGE under reducing conditions and transferred electophoretically to nitrocellulose filters. Unspecific binding of antibody was blocked by incubating with 3% BSA for 2 hrs. Immunoblotting was carried out with rabbit anti-trk A receptor (or the appropriate antibody for the growth factor receptor of interest) followed by peroxidase conjugated secondary anti-immunoglobulin antibodies, and the blots were developed by enhanced chemiluminescence method (ECL, Amersham). Western blots of cell culture lysates (FIG. 6) provided preliminary evidence that BDNF+RA+N5 (column 4) resulted in the highest expression of nestin-ir and NeuN-ir in human BMSC.

Moreover, cells removed from the flask bottom as above (BMSC), or separated by magnetic cell sorting, were replated in 35 mm culture dishes in the presence of a neuronal growth medium (N5) supplemented with 5% horse serum, 1% FBS, transferrin (100 μg/ml), putrescine (60 μM), insulin (25 μg/ml), progesterone (0.02 μM), selenium (0.03 μM), 9-cis retinoic acid or all trans retinoic acid (RA) (0.5 μM), and any one of several neuronal growth factors at a concentration of 1–10 ng/ml (Brain Derived Growth Factor-BDNF, Glial-derived Neurotrophic Factor-GDNF, or Nerve Growth Factor-NGF). After 7 to 14 days, some of the BMSC had changed morphology and developed the phenotype of neurons, glia and fibroblasts.

Example 6

Effects of Co-culturing Human BMSC with Rat Fetal Striatal Cultures

Mouse BMSC conditioned with RA and BDNF were co-cultured with primary neuronal mesencephalic cells prepared from E15 fetal rats. Human BMSC were established using the methods described above. Cells were labelled with 10 μM concentration of fluorescent green "cell tracker" (5-chloromethyl fluorescein diacetate, Molecular Probes, Inc.), and plated on a cell bed of rat fetal striatal cells prepared three days earlier. Cultures were fed with RA (0.5 μM)+BDNF (10 ng/ml) in N5 medium. After 10 days in culture, cells were processed for immunocytofluorescence using primary antibodies against NeuN, GFAP, nestin and fibronectin followed by Texas red fluorescence-labeled secondary antibody. This permitted a dual labelling of cells to determine whether cells which exhibited specific markers for neurons, glia or neuroectoderm also had a bone marrow origin. See FIGS. 7A–7F. FIG. 7A shows cell immunoreactive for the neuronal marker (NeuN). FIG. 7B shows the glial cell marker (GFAP). FIGS. 7C and 7D show the corresponding areas with green-labeled cells (Cell Tracker-labeled BMSC). FIGS. 7E and 7F show cells that were doubly labelled (yellow color). Interestingly, two of the NeuN-ir cells were of BMSC origin, and one of the GFAP-ir cells was of BMSC origin. These data provide additional evidence that BMSC of human as well as of mouse origin were capable of differentiating into cells with neural phenotypes.

LacZ-labelled BMSC co-cultured with primary rat mesencephalic cultures differentiated into neuron-like cells co-labeled with NeuN-ir and β-gal.

Example 7

In Vivo

Mouse lacZ BMSC were grafted into denervated corpus striatum of rats previously lesioned with 6-OH-dopamine and into unlesioned rats. One and three months later, rats were sacrificed, and brains were processed for histochemistry and immunocytochemistry. BMSC-derived cells were visualized by β-gal+staining or by anti-mouse antibodies directed against mouse major histocompatibility antigen type I. Expression of neuronal markers in BMSC-derived cells was determined by their immunoreactivity to antibodies against neuron-specific nuclear antigen (NeuN-ir), tyrosine hydroxylase (TH), microtubule associated protein (MAP2), neurofilament (NF), and calbindin (CB).

BMSC-derived cells grafted into striatum did not remain localized to the striatum where they were grafted, but were found in midbrain, thalamus and rarely in cerebellum when identified by anti-N mouse antibody. Some of these mouse BMSC co-expressed NeuN-ir or TH-ir. Both grafted and control ungrafted rats exhibited β-gal+cells in similar and distinct distributions. β-gal+cells were found in olfactory bulb, supraoptic and paraventricular hypothalamus, the red nucleus, third nerve nucleus, s. nigra, and were distributed in the cerebellum in a pattern identical to Purkinje cells in ungrafted rats.

BMSC, conditioned with RA and BDNF, expressed neuronal markers and decreased expression of stromal and fibroblastic markers. When conditioned lacZ BMSC were co-cultured with primary mesencephalic neurons, many BMSC-derived cells co-expressed NeuN-ir and β-gal. When grafted into denervated striatum, conditioned BMSC expressed several neuronal markers and migrated from the site of grafting to both sides of thalamus, and to a lesser extent hippocampus, and to the unlesioned s. nigra. Positive staining for β-gal activity in ungrafted rats gave rise to an artefact that could easily be mistaken for β-gal BMSC. However, a second marker for BMSC confirmed that these cells migrated and differentiated into a neuron-like cell.

Example 8

In vivo Data Showing that BMSC Differentiate Into Neural Cells (Neurons or Glia) Using a Third Marker of the BMSC Previous examples used β-gal+BMSC from mice, and antibodies specific to mice. In this experiment, mouse BMSC were pre-labeled with red fluorescent PKH26 (Sigma, Inc.) or Cell Tracker Orange (Molecular Probes, Inc.) before grafting into denervated rat striatum as described above. Two weeks after grafting, fluorescent BMSC had migrated from the site of the graft (some to the cerebral cortex on the contralateral side). After only two weeks, a small proportion of grafted cells had begun expressing neural markers such NeuN-ir and GFAP-ir (FIGS. 8 and 9). Mouse BMSC labelled with red PKH26 also express the neuron marker NeurN (green fluorescence—FIG. 8). In addition, the morphology of the doubly labeled cells is that of neurons. Image was produced with a Zeiss LSM510 confocal scanning microscope. In FIG. 9, there is a doubly labeled glial cell with the red fluorescent tracer identifying it as a BMSC-derived cell and the green fluorescence is due to GFAP-ir. Note the morphology is that of a glial cell.

Industrial Applicability

Examination of brain tissue sections in the above experiments revealed regenerating BMSC-derived β-gal+cells in multiple brain regions distant from the site of implantation in the corpus striatum. The migration of the treated BMSCs includes, but is not limited to, the following brain regions:

mitral cell zone of the olfactory bulb, paraventricular and supraoptic nuclei of hypothalamus, hippocampus, habenula, oculomotor nucleus, red nucleus, s. nigra, abducens, facial and hyoglossal cranial nerve nuclei, inferior olive of medulla, ventral horn of the spinal cord and the cerebellar Purkinje cell layer. The BMSC β-gal+cells assumed multiple phenotypes including epithelial-like cuboidal cells in choroid plexus; small oligodendroglial-like cells in optic chiasm and sub-cortical white matter; large neuron-like cells in the red nucleus, s. nigra, and brainstem motor nuclei. This novel method of neural transplantation is a scientifically feasible and clinically promising approach to the treatment of neurodegenerative diseases and stroke, as well as for repair of traumatic injuries to brain and spinal cord.

There are numerous uses for BMSC in university and pharmaceutical discovery laboratories. Human BMSC which migrate to the cerebellum in the rat model and assume the characteristics of Purkinje cells can be used to test the effects (both therapeutic and toxic) of drugs on human cerebellar cells. Likewise, human BMSC implanted in other areas of the brain that assume the characteristics of those cells also can be used for testing drug toxicity and therapeutic efficacy in a wide variety of disorders. Before implantation, the cells can be genetically engineered to carry the genes which have been implicated in various brain and nervous system disorders.

One potential use of the migratory and regenerative nature of the BMSCs is treatment of Parkinson's Disease. The pretreated BMSCs can replace fetal neurons that have been used for transplantation in that condition. The BMSCs treated with retinoic acid and BCNF have been shown to migrate to the substantia nigra, where a dopaminergic neuron deficit causes PD. The delivery of BMSCs to the substantia nigra could help regenerate the nigral neurons and return the flow of dopamine to that region.

The regeneration of the cerebellar Purkinje cell layer can help improve coordinated movement of the patient. Restoration of the cerebellum would be useful in cerebellar tumors, typically a medulloblastoma that occurs in childhood. In adults, a similar syndrome may be seen in chronic alcoholism, which causes degeneration of the vermis. The patient has an unsteady, staggering ataxic gait; he or she walks on a wide base and sways from side to side. Barr, M. L. and Kiernan, J. A. *THE HUMAN NERVOUS SYSTEM, AN ANATOMICAL VIEWPOINT*, 6$^{th}$ ed., J. B. Lippincott Company, Philadelphia (1993).

Another use for the migration and regeneration of BMSCs is in the mitral cell zone of the olfactory bulb. Impulses from the olfactory bulb are conveyed to olfactory areas for subjective appreciation of odors and aromas. Barr, M. L. and Kiernan (ibid.) The migration and regeneration of BMSCs to this brain region could treat loss of taste from toxic chemicals, aging and injury.

Administering the BMSCs can be used in the regeneration of facial and hyoglossal cranial nerve nuclei and restoration of movement of facial muscles after a stroke or other injury.

Administering the BMSCs could aid in the regeneration of the ventral horn of the spinal cord and restoration of motor skills lost from trauma to the spine.

Administering the BMSCs could aid in the regeneration of an injured hippocampal region.

What is claimed is:

1. A method for producing cells with a neuronal phenotype from bone marrow cells, said method comprising the steps of
   a) harvesting the bone marrow;
   b) selecting from the bone marrow a plurality of bone marrow stromal cells by stromal cell adherence to a surface;
   c) resuspending the adherent stromal cells in a growth medium with a mitogen selected from EGF, PDGF or a combination thereof, and optionally repeating this step at least one time;
   d) incubating the cells from step c in neuronal growth medium including at least a retinoic acid and at least one differentiating agent selected from BDNF, GDNF or NGF, thereby producing cells with a neuronal phenotype.

2. The method of claim 1 wherein step b further comprises separating out and discarding hematopoietic stem cells that express CD34.

3. The method of claim 1 wherein step b further comprises placing the bone marrow cells and suitable culture medium in a plastic culture medium container, allowing the bone marrow stromal cells to adhere to the plastic, and removing the other cells by replacing the medium.

4. The method of claim 1 wherein in addition to the differentiating agent fetal neuronal cells are added.

5. The method of claim 1 wherein the retinoic acid is 9-cis retinoic acid, all-trans retinoic acid or a combination thereof.

* * * * *